(12) United States Patent
Farber et al.

(10) Patent No.: US 8,124,056 B2
(45) Date of Patent: *Feb. 28, 2012

(54) HIGH THROUGHPUT GENETIC SCREENING OF LIPID AND CHOLESTEROL PROCESSING USING FLUORESCENT COMPOUNDS

(75) Inventors: Steven Farber, Baltimore, MD (US); Michael Pack, Philadelphia, PA (US); Marnie Halpern, Pikesville, MD (US)

(73) Assignees: Trustees of the University of Pennsylvania, Philadelphia, PA (US); Carnegie Institution of Washington, Washington, DC (US)

( * ) Notice: Subject to any disclaimer, the term of this patent is extended or adjusted under 35 U.S.C. 154(b) by 163 days.

This patent is subject to a terminal disclaimer.

(21) Appl. No.: 12/362,698

(22) Filed: Jan. 30, 2009

(65) Prior Publication Data

US 2009/0136428 A1 May 28, 2009

Related U.S. Application Data

(60) Division of application No. 10/341,538, filed on Jan. 13, 2003, now Pat. No. 7,488,467, which is a continuation of application No. 09/974,550, filed on Oct. 10, 2001, now abandoned.

(60) Provisional application No. 60/238,928, filed on Oct. 10, 2000, provisional application No. 60/264,977, filed on Jan. 30, 2001.

(51) Int. Cl.
*A61K 49/00* (2006.01)

(52) U.S. Cl. ......... 424/9.2; 424/1.11; 424/1.65; 424/9.1

(58) Field of Classification Search .............. 424/1.11, 424/1.37, 1.65, 1.73, 1.81, 1.85, 1.89, 9.1, 424/9.2; 436/71
See application file for complete search history.

(56) References Cited

U.S. PATENT DOCUMENTS

| | | | |
|---|---|---|---|
| 4,789,633 A | 12/1988 | Huang et al. | 435/458 |
| 6,299,858 B1 | 10/2001 | Serbedzija et al. | 424/9.2 |
| 6,703,214 B2 * | 3/2004 | Verwaerde et al. | 435/19 |
| 7,488,467 B2 | 2/2009 | Farber | |
| 2002/0049986 A1 | 4/2002 | Farber | |
| 2002/0137205 A1 * | 9/2002 | Verwaerde et al. | 435/400 |
| 2003/0129670 A1 | 7/2003 | Tsien et al. | 435/7.2 |

OTHER PUBLICATIONS

Pack, M. et al., 1996, "Mutations affecting development of zebrafish digestive organs", Development (Cambridge), 123(1):321-328.
Kamisaka et al (1999), Biochimica et Biophysica Acta, vol. 1438, pp. 185-198.
Hendrickson et al (Analytical Biochemistry, 1999, vol. 276, pp. 27-35).
Farber et al (The Journal of Biological Chemistry, 1999, vol. 274, No. 27, pp. 19338-19346).
Ikeda et al (Journal of Nutrition, 1989, vol. 119, No. 10, pp. 1383-1387).

* cited by examiner

*Primary Examiner* — D L Jones
(74) *Attorney, Agent, or Firm* — Montgomery, McCracken, Walker & Rhoads, LLP; Evelyn H. McConathy

(57) ABSTRACT

The present invention utilizes fluorescent lipids, particularly quenched phospholipid or cholesterol analogues, to facilitate screening for phenotypes representing perturbations of lipid and/or cholesterol processing in a vertebrate; screening for genetic mutations that lead to disorders of phospholipid and/or cholesterol metabolism; and screening of compounds designed to treat disorders of phospholipid and/or cholesterol metabolism in the vertebrate.

20 Claims, 13 Drawing Sheets

HIGH THROUGHPUT GENETIC SCREENING OF LIPID AND CHOLESTEROL PROCESSING USING FLUORESCENT COMPOUNDS

CONTINUING APPLICATION DATA

The present application is filed as a Divisional Application of U.S. Ser. No. 10/341,538, filed on Jan. 13, 2003, and issued into U.S. Pat. No. 7,488,467, which was a Continuation of U.S. Ser. No. 10/062,225, filed on Jan. 30, 2002, now Abandoned, which was a Continuation of U.S. Ser. No. 09/974,550, filed on Oct. 10, 2001, now Abandoned, which claims priority under 35 U.S.C. §119 based upon U.S. Provisional Application No. 60/238,928 filed Oct. 10, 2000 and in-part based upon U.S. Provisional Application No. 60/264,977 filed Jan. 30, 2001.

FIELD OF THE INVENTION

The present invention generally relates to the fields of biochemistry and pharmacology and to the use of a genetic model organism labeled with fluorescent lipids to screen for drugs and genetic alterations related to phospholipid and/or cholesterol metabolism and, more particularly, to the use of optically clear zebrafish in conjunction with tagged or quenched lipids for studying lipid metabolism in vivo.

BACKGROUND OF THE INVENTION

Genetic analysis in zebrafish is a powerful approach for identifying genes that direct vertebrate development (1-3). Since the completion of the large-scale chemical mutagenesis screens in 1997, the phenotypic and molecular characterizations of many mutations have been reported (4-16).

Analyses of mutations that affect early developmental processes, such as the specification of the embryonic axes and germ layers, have been particularly rewarding (7, 10, 17-27). Recently, related work with mutations that affect organogenesis has led to the recognition that the zebrafish is an important model system for biomedical research (28-31). Given the many aspects of organ physiology that have been conserved during vertebrate evolution, genetic screening to assay organ function in the optically transparent zebrafish is a valuable approach to understanding a variety of metabolic processes and disorders in vertebrates.

By zebrafish chemical mutagenesis screening, nine recessive lethal mutations that perturb development of the digestive organs were identified (2, 31). Although the mutants were identified using morphological criteria, their phenotypic analysis suggests that in some cases the affected genes regulate developmental processes that are relevant to digestive physiology and other aspects of vertebrate metabolism.

Through the analysis of these and other zebrafish mutants, the limitations inherent to genetic screens that are based solely on morphological criteria became apparent. First, not all organs are readily distinguished in zebrafish larvae, and mutations that perturb organ morphology are often overlooked. Second, since it is difficult to visualize specific cell populations within many larval organs, mutations that affect the development or function of these cells can be overlooked as well. Third, despite the transparency of the zebrafish larva, the function of few organs can be effectively assayed by visual inspection alone.

For these reasons, it was concluded that, in most instances, morphology-based screens are best suited for the identification of genes that regulate specification and patterning of embryonic structures. By contrast, screens designed to address biomedical concerns are most effective when they assay physiological processes directly.

Within the past few years, the discovery and analysis of zebrafish mutants affecting organogenesis has confirmed an important role for the zebrafish in biomedical research. The ability to apply high throughput genetic analyses to vertebrate organ physiology using this model system is unprecedented and will undoubtedly, over time, lead to the discovery of many genes that regulate vertebrate organ development and physiology. Such zebrafish research will complement research in other vertebrate model systems.

By conducting a mutagenesis screen using fluorescent lipids, an undertaking not feasible with standard zebrafish screening strategies, the power of high throughput genetic analysis can be applied to lipid metabolism. This has important implications for human diseases such as, but not limited to, cancer, inflammatory and cardiovascular diseases, and congenital and acquired diseases of the intestine and liver.

The fluorescent phospholipase $A_2$ ($PLA_2$) substrates described in the present invention are the first prototypes in this class of reagents. Although lipid metabolism in the digestive tract is complex and involves multiple organs the present invention discloses a method of assaying this pathway since gall bladder fluorescence represents one of the last steps in lipid processing. Because they serve as reporters of lipid processing, the fluorescently-tagged reagents of the instant invention provide a sensitive assay for a wide range of digestive developmental and physiological processes including, but not limited to, swallowing; lipid digestion, absorption, and transport; esophageal sphincter function; intestinal motility; organogenesis of the mouth and pharynx, esophagus, intestine, liver, gallbladder and biliary system, and exocrine pancreas and ducts; and the cellular and molecular biology of $PLA_2$ regulation, polarized transport, and secretion.

Given the shared features of lipid processing in mammals and teleosts (82, 105), zebrafish mutagenesis screens using lipid reporters can be used to identify genes with functions relevant to human lipid metabolism and disease. Moreover, since both mammals and teleosts metabolize lipids in an analogous manner, the high throughput screens and fluorescent lipids disclosed in the instant invention can be employed using a variety of vertebrate model systems, including but not limited to, rodents, amphibia, and fish. The present invention involves utilizing fluorescent lipids to screen for phenotypes representing perturbations of lipid processing; to screen for mutations of specific genes that lead to disorders of phospholipid and/or cholesterol metabolism; and to screen for compounds designed to treat disorders of phospholipid and/or cholesterol metabolism, such as, but not limited to cancer, inflammatory and cardiovascular disease, and congenital and acquired diseases of the intestine and liver.

ABBREVIATIONS

"$PLA_2$" means "phospholipase $A_2$"
"$PLA_1$" means "phospholipase $A_1$"
"PLB" means "phospholipase B"
"PLD" means "phospholipase D"
"PED6" means "N-((6-(2,4-dinitrophenyl)amino)hexanoyl)-1-palmitoyl-2-BODIPY-FL-pentanoyl-sn-glycero-3-phosphoethanolamine"
"hpf" means "hour post-fertilization"
"dpf" means "day post-fertilization"
"FRET" means "fluorescence resonance energy transfer"
"PC" means "phosphatidylcholine"

"TLC" means "thin layer chromatography"
"cPLA$_2$" means "cytoplasmic PLA$_2$"
"sPLA$_2$" means "secretory PLA$_2$"
"COX" means "cyclooxygenase"
"APC" means "adenomatous polyposis coli"
"EP" means "early pressure"
"ENU" means "ethylnitrosourea"
"WT" means "wild-type"
"SLR" means "single locus rate"
"IVF" means "in vitro fertilization"
"BAC" means "bacterial artificial chromosome"
"PAC" means "P1-derived artificial chromosome"
"YAC" means "bacterial artificial chromosome"
"SSR" means "simple sequence report"
"CSGE" means "conformation sensitive gel electrophoresis"
"VLDL" means "very low density lipoprotein"
"EM" means "embryo medium"
"NBD cholesterol" means "nitrobenzoxadiazole cholesterol"

DETAILED DESCRIPTION

Figure 1:
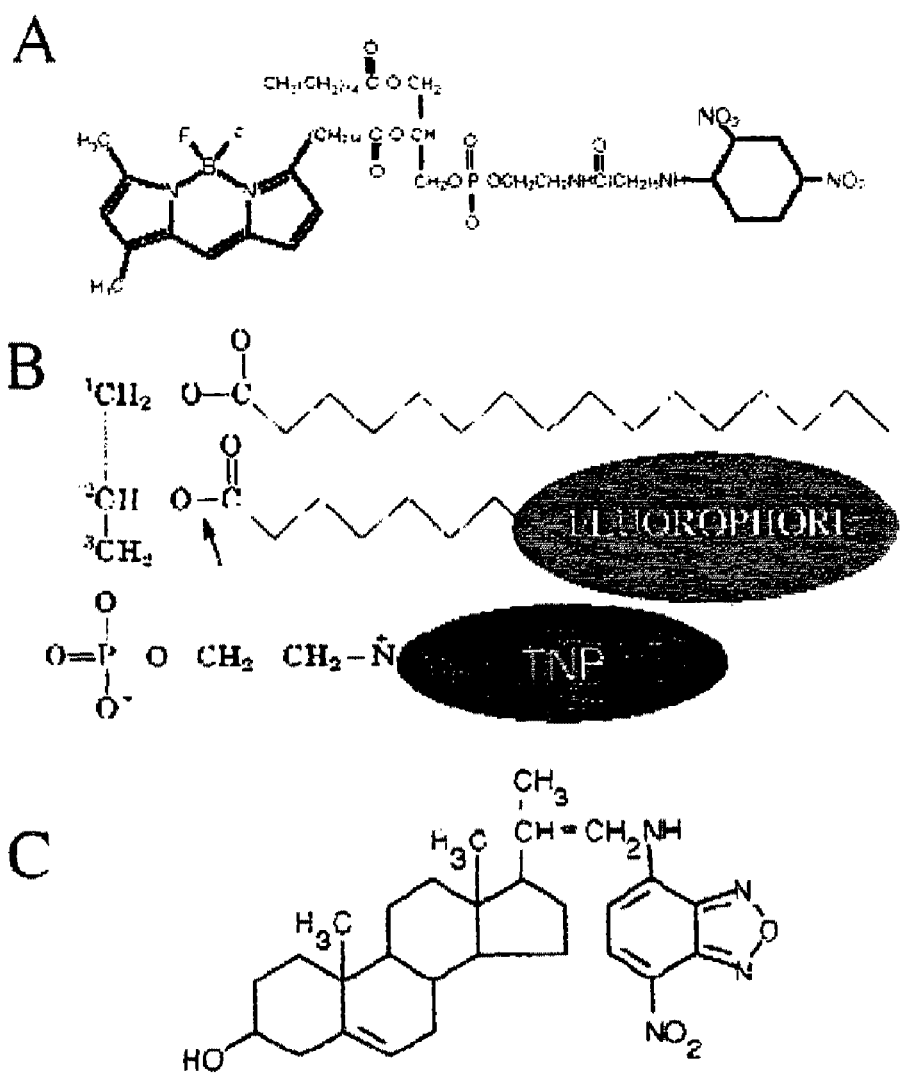
FIG. 1. Schematic of PED6, a quenched PLA$_2$ substrate. A. The dinitrophenol on the phospholipid headgroup effectively quenches any emission resulting from excitation at 505 nm of the BODIPY-labeled acyl chain. B. When the BODIPY-labeled acyl chain is liberated by PLA$_2$ mediated cleavage, the quencher is separated from the fluorophore and emission (515 nm) is observed. C. NDB-labeled cholesterol in which the fluorophore replaces the terminal segment of cholesterol's alkyl tail.

The present invention relates to a mutagenesis screen to identify genes that regulate lipid metabolism using fluorescently-tagged or quenched lipids such as cholesterol or lipids that are substrates for phospholipases such as PLA$_2$. For example, cleavage of quenched phospholipid substrates by PLA$_2$ results in an increase in fluorescence intensity or alters the spectral properties of fluorescent emission thus allowing lipid metabolism to be followed in vivo. In one embodiment of the instant invention, optically transparent zebrafish larvae exposed to the fluorescently-tagged or quenched lipids display intense gallbladder fluorescence, which reflects lipid cleavage by intestinal PLA$_2$ and subsequent transport of the fluorescent cleavage products through the hepatobiliary system.

The instant invention presents evidence demonstrating that in the context of a mutagenesis screen, fluorescent PLA$_2$ substrates and fluorescently-tagged cholesterol or other lipids have the potential to identify genes that affect many aspects of lipid metabolism. Consequently, when used in the context of a genetic screen these reagents provide a high throughput readout of digestive physiology that cannot be assessed using standard screening strategies. Given current understanding of the pathway of lipid processing in zebrafish, specifically its shared features with lipid processing in mammals, the present invention has relevance for biomedical research related to, among other things, cancer, inflammatory and cardiovascular diseases, and congenital and acquired diseases of the intestine and liver.

Fluorescent Reagents to Assess Organ Physiology In Vivo

The fluorescent lipids of the instant invention allow assaying of physiological processes. The reagents are fluorescent analogues of compounds that could serve as modifiable substrates in important metabolic and signaling pathways. The reagents of the instant invention were constructed by covalently linking fluorescent moieties to sites adjoining the cleavage site of phospholipids. Dye-dye or dye-quencher interactions modify fluorescence without impeding enzyme-substrate interaction (106). PLA$_2$ cleavage results in immediate unquenching and detectable fluorescence. Quenched phospholipids [N-((6-(2,4-dinitrophenyl)amino)hexanoyl)-1-palmitoyl-2-BODIPY-FL-pentano-yl-sn-glycero-3-phosphoethanolamine (PED6)] allow subcellular visualization of PLA$_2$ activity and reveal organ-specific activity (36). The evidence presented in the instant invention demonstrates that zebrafish larvae 5 days post-fertilization (dpf) bathed in PED6 show intense gall bladder fluorescence and, shortly thereafter, intestinal luminal fluorescence. Substrate modification allows localization of enzymatic activity by altering the emission spectrum of the fluorescent compounds. When used in the context of a genetic screen these fluorescent lipids provide a high throughput readout of organ function.

The reagents of the instant invention facilitated the development of genetic screens that are more sensitive than the whole-mount in situ and antibody based screening protocols now used to assay gene expression. The fluorescent reagents are simpler to use since they can be administered to and assayed in a wide range of organisms, including, but not limited to rodents and teleosts, and they offer the opportunity to screen for hypomorphic mutations that alter gene function but do not affect levels of gene expression. By providing a visual assay of metabolic processes, these reagents can be used to identify mutations that affect more than just the single gene responsible for substrate modification. Visualization of the fluorescent signal also is dependent upon the delivery and uptake of the substrate as well as the storage, metabolism or secretion of its modified metabolites.

Fluorescent PLA$_2$ Substrates

PLA$_2$s were chosen as the "target" enzymes to assay because of the important role these enzymes play in the generation of lipid signaling molecules (32-34). PLA$_2$s are a large family of enzymes that can be categorized according to their cellular distribution, molecular weight, and calcium dependence (33). Some PLA$_2$s also exhibit a preference for phospholipids with arachadonyl sn2 acyl side chains (34, 37, 38). Given the wide range of processes the PLA$_2$ family of enzymes is known or thought to regulate, the advantage of the fluorescent lipids as screening reagents is significant.

cPLA$_2$. For example, one PLA$_2$ gene family member, cytoplasmic PLA$_2$ (cPLA$_2$), regulates eicosanoid production. Eicosanoids are ubiquitous signaling molecules generated by the biochemical modification of arachidonic acid, the principal fatty acid liberated from membrane phospholipids by cPLA$_2$s (42-44). cPLA$_2$s have a strong preference for arachidonyl phospholipids and cPLA$_2$ cleavage of these phospholipids is known to be the rate-limiting step in eicosanoid synthesis (39, 41, 44-47). In comparison, secretory PLA$_2$s (sPLA$_2$s) exhibit little substrate preference and unlike cPLA$_2$, the arachidonic acid generated through s PLA$_2$ activity is not directly coupled to eicosanoid production (37, 46).

The two major classes of eicosanoids produced by vertebrate cells are leukotrienes and prostaglandins (48, 54). Prostaglandins are a large family of signaling molecules that are synthesized through the action of cyclooxygenases (COX) and prostaglandin-isomerases on PLA$_2$ generated arachidonic acid (48). Prostaglandins are especially important in vertebrate physiology as they regulate a myriad of physiological processes, including hemostasis, cell proliferation, fertility, and inflammation (48-50). The importance of prostaglandin in humans is underscored by the widespread use of COX inhibitors (e.g., aspirin) as medicinal agents.

Given the focus of this invention, there is special interest in intestinal prostaglandins. Intestinal prostaglandins play an important role in regulating mucosal blood flow (51-54), and inhibition of prostaglandin synthesis by COX inhibitors, such as aspirin, is associated with the development of mucosal ulcerations (55). There is also strong evidence that intestinal prostaglandins regulate epithelial cell proliferation (56-58). COX inhibitors are known to have a chemopreventitive effect on several human digestive cancers, and COX-2 has been identified as a genetic modifier of APC, an important colon cancer gene.

Because arachidonic acid release is the rate-limiting step in eicosanoid production, characterization of the cell specific regulation of cPLA$_2$s is important (33, 34). Although the genes in some of the signaling pathways that activate cPLA$_2$ have been identified, this characterization is far from complete. A screen utilizing fluorescent lipid substrates will allow identification of mutations that perturb lipid processing and alter cPLA$_2$ activity.

sPLA$_2$. Another PLA$_2$ gene family member, s PLA$_2$, plays a role in inflammation, host defenses, digestion, and cell proliferation (43, 70, 71). In comparison to cPLA$_2$s, s PLA$_2$s show little preference for arachidonic acid over other phospholipids sn2 acyl side chains (34).

There is a large body of experimental and clinical evidence supporting the role of sPLA$_2$s in inflammation. First, serum levels of sPLA$_2$ are increased in inflammatory conditions such as Rheumatoid Arthritis, Crohn's Disease, endotoxic shock, and atherosclerosis (32, 72-76). Second, sPLA$_2$ cleavage of arachidonyl phospholipids has been shown to augment cPLA$_2$ mediated eicosanoid production (46, 71, 77). Third, independent of its enzymatic activity, sPLA$_2$ has been shown to bind to a specific cellular receptor that plays a role in endotoxic shock (78) and other aspects of the inflammatory response (43, 79, 80). Like cPLA$_2$, the regulation of inflammatory sPLA$_2$s (Groups II and V) is an important area of biomedical research.

Group IIA sPLA$_2$ recently has been shown to play a role in colon cancer tumorigenesis through its genetic interaction with APC in the min mouse, a colon cancer animal model (66-68). High levels of this gene are expressed in intestinal Paneth cells where it is also believed to function as an antimicrobial agent because of its ability to digest bacterial cell wall phospholipids (38, 76, 81). The precise mechanism of sPLA$_2$'s mitogenic effect is unclear. Since COX activity also has been shown to modify colon tumorigenesis in the min mouse, sPLA$_2$ may be acting via prostaglandins (69). This hypothesis is counter-intuitive, however, because in the min mouse, loss of sPLA$_2$ function is associated with a tumor promoting effect. An alternate hypothesis suggests that in the colon, sPLA$_2$ also may function as a cell-signaling molecule, independent of its enzymatic activity, through its interaction with the sPLA$_2$ receptor.

The role of sPLA$_2$s in the digestion and absorption of dietary phospholipids has been studied in many vertebrate species, including teleosts (82). Pancreatic sPLA$_2$ is the prototypical low molecular weight sPLA$_2$-its proenzyme is secreted into the intestinal lumen where it is activated and cleaves dietary phospholipids that have been modified by bile salts (83). sPLA$_2$ activity also is present in the intestinal brush border and undoubtedly contributes to the digestion of dietary phospholipids (84, 85). Intestinal PLA$_2$ activity is present in the form of PLB, an enzyme that can function as a high molecular weight, calcium independent PLA$_2$ as well as a lysophospholipase (86-89). Regulation of lipid absorption and transport is an important area of biomedical research that has implications for metabolic, inflammatory, and cardiovascular diseases.

Phospholipid Metabolism

In fish, like mammals, dietary phospholipid is cleaved by intestinal and pancreatic PLA$_2$s to form free fatty acid, lysolipid, and phosphoglycerol (82). These molecules are absorbed by enterocytes, presumably by simple diffusion (lysolipid, phosphoglycerol) and receptor mediated processes (fatty acid) (90). Within the enterocyte, the free fatty acids are processed according to their size: long carbon chain fatty acids are re-esterified to form triglycerides and phospholipids, packaged into lipoprotein particles (chylomicrons or VLDL) and enter the general circulation via the lymphatics; shorter chain fatty acids presumably can enter the circulation directly via the portal vein (90-92). Lipoprotein bound phospholipids enter cells in the periphery by binding to specific receptors or via endocytosis (90, 91).

In comparison to the fatty acids, the fate of the phospholipid derived lysolipid and phosphoglycerol cleavage products are less certain. In mammals, they are largely re-esterified to form phospholipids, which then are incorporated into lipoproteins and absorbed via the lymphatics, like triglycerides (90-92). Vertebrate lipid absorption is further complicated by the existence of other intestinal phospholipases (PLD, PLA$_1$) that cleave the polar head group or sn1 fatty acid from lysolipids and phospholipids. This raises the possibility that phospholipids undergo extensive re-arrangement within the intestinal epithelium prior to absorption. In fish, there is experimental evidence supporting this observation (82).

Materials, Methods, and Results

Zebrafish:

Zebrafish, Danio rerio, were housed in a separate facility consisting of approximately 500 tanks of varying sizes (1 liter, 3.75 liter, and 9 liter). Environmental conditions were carefully monitored for disease prevention and to maintain fish in perpetual breeding condition. Male and female fish were reared at a density of no more than 8 fish per liter at a constant temperature and light cycle (27-29° C. with the light/dark cycle kept at $^{14}/_{10}$ hours) in pre-treated water (heated, charcoal-filtered and UV-sterilized). Fish were fed twice daily with a variety of dried and live foods.

Zebrafish provide a relatively simple model system for more complex vertebrates, such as humans. They are small in size, easy to maintain and breed, and produce large numbers of progeny on a daily basis. Their embryos develop rapidly and are optically clear, permitting direct observation of the developing digestive system. Being vertebrates, zebrafish contain orthologues for almost all human genes. The species also is amenable to genetic methods so that one can screen for mutations that disrupt organ function or development. It is possible, therefore, to identify genes important for intestinal development and function by examining fish that carry random mutations. In addition, many techniques have been worked out for manipulating zebrafish, including in vitro fertilization, production of haploids and parthenogenic diploid embryos, mutagenesis, cell lineage and cell transplantation.

Generation of Fluorescent PLA Substrates to Assay Lipid Processing:

In the instant invention, a family of fluorescent phospholipids was generated with such phospholipids serving as substrates for PLA$_2$. As previously noted, characterization of the genetic regulation of PLA$_2$ is an active area of biomedical research (67, 68), and the reagents described were developed to function as in vivo biosensors of PLA$_2$ activity that can be assayed using microscopy or simple biochemical techniques. When administered to zebrafish embryos and larvae, these reagents provide a rapid readout of a wide range of developmental and physiological processes that are amenable to high throughput genetic analyses. The fluorescent lipids described in this proposal are quenched fluorescent phosphatidylcholine analogues and NBD-labeled cholesterol (FIG. 1). The phospholipid reagents differ in both their fluorescent emission and their specificity for different PLA$_2$ isoforms (93, 94). Cleavage of these phospholipids by PLA$_2$ generates a fluorescent fatty acid or lysolipid that can be used to localize and quantify PLA$_2$ activity in live fish (36, 94). It has been demonstrated that there is utility of these agents for revealing localized PLA$_2$ activity in developing zebrafish embryos (94).

Figure 2:
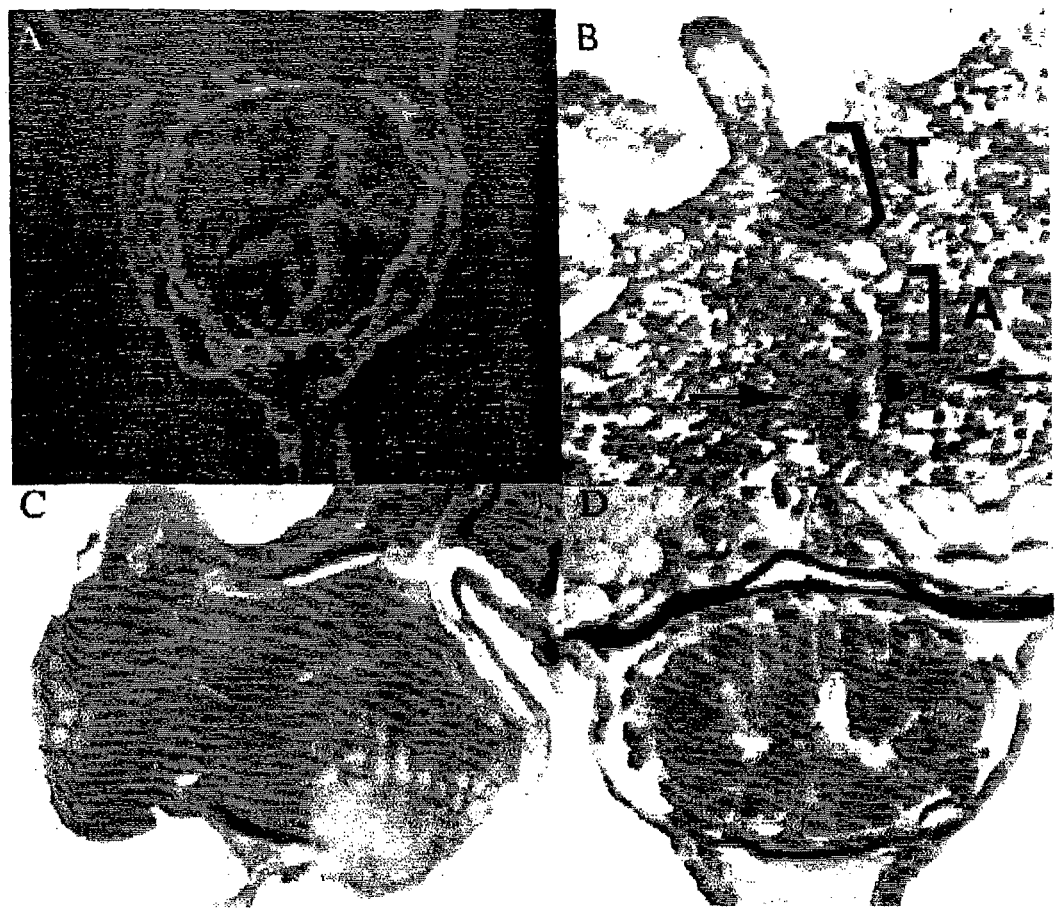
FIG. 2. Intestinal differentiation in 84 hpf larvae. A. Cross-section of posterior intestine. Desmin immunoreactivity of intestinal smooth muscle (green) and enteric neurons as indicated by zn6 immunoreactivity (red) demonstrate development of the enteric neuromuscular system. B. Transmission Electromicrograph showing mature apical junctional complexes in enterocytes in the intestinal epithelium. Arrow points to desmosomes; A: Adherens junction. T: tight junction. C. Histochemical detection of enterocyte aminopeptidase activity (red); anterior intestinal cross section. D. Histological detection of goblet cell mucin (purple) in the posterior intestine. Also present at this developmental stage, immunoreactive pancreatic polypeptide in enteroendocrine cells.
Figure 3:
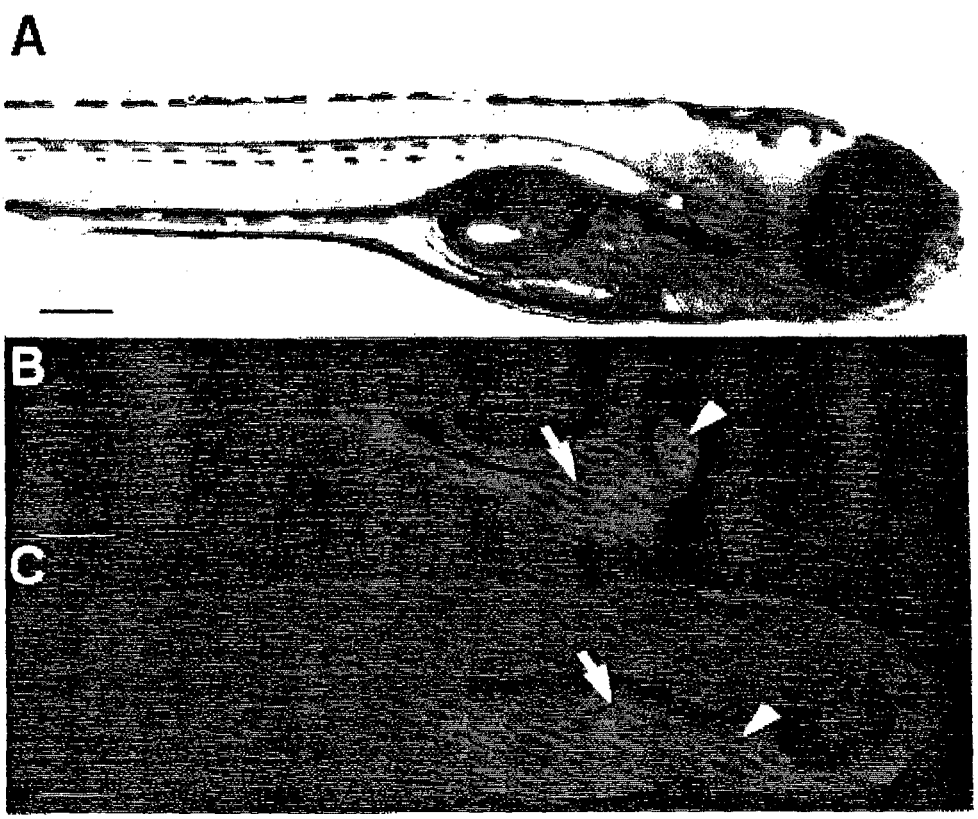
FIG. 3. PED6: a fluorescent lipid reporter. A. Bright-field image of a 5 dpf larva soaked in PED6 (3 μg/ml, 2 hr). B. Corresponding fluorescent image, with intestinal (arrow) and gall bladder (arrowhead) labeling. C. Larva soaked in BODIPY-C5-PC (0.2 μg/ml). In contrast to B, unquenched fluorescent lipid labels the pharynx (arrowhead), confirming that lipid is swallowed before gall bladder labeling (arrow).

To determine whether these reagents could be used to study organ specific PLA$_2$ activity, the quenched fluorescent lipids were administered to zebrafish larvae at 5 dpf, a developmental stage when the major larval organ systems function (FIG. 2). 5 dpf larvae soaked in PED6 uniformly developed intense gallbladder fluorescence 15-20 minutes after ingesting the lipid (FIG. 3). Based upon established mechanisms of vertebrate lipid processing, it was theorized that the larval gallbladder fluorescence reflected ingestion of the lipid reagents followed by intestinal PLA$_2$ cleavage, intestinal absorption, transport to the liver and biliary excretion of the fluorescent cleavage product.

Figure 4:
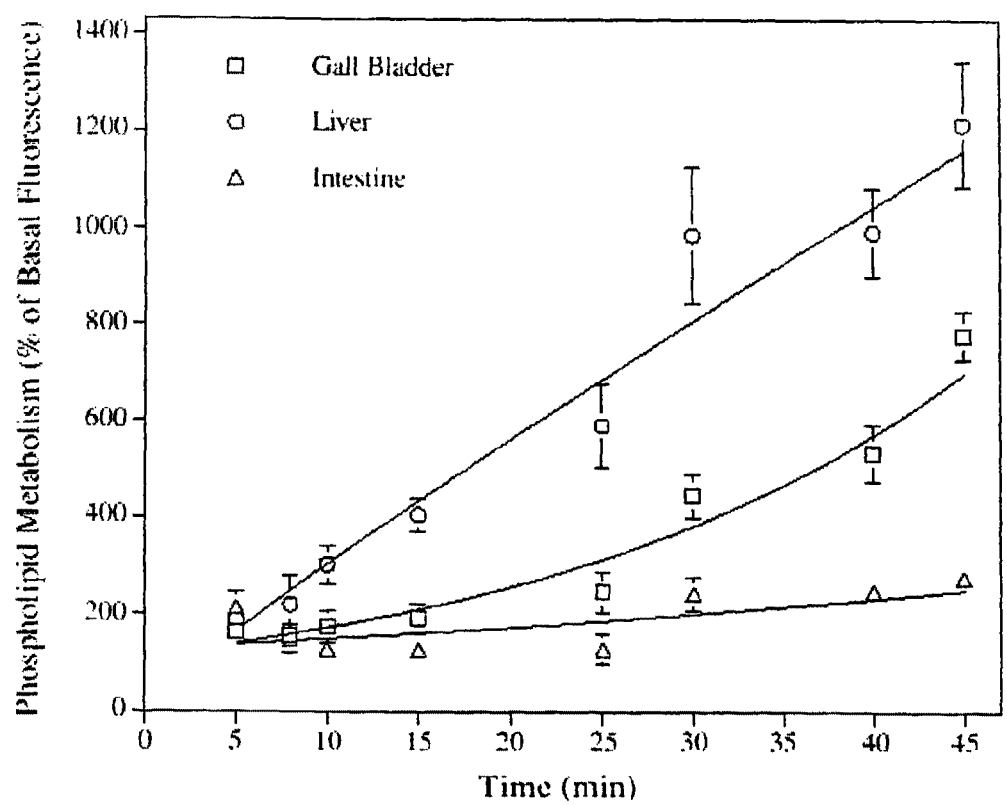
FIG. 4. Rate of fluorescence after PED6 labeling. Larvae (n=5) were placed in medium containing PED6 (0.17 mg/ml) and tricaine. Images were captured at various times and fluorescence intensity was determined in specific structures. Organ fluorescence intensity determined at specific times was normalized to the observed intensity at 45 min. Data are expressed as Mean.+-.SEM.

This hypothesis was tested with three experiments. First, to establish that PED6 is swallowed by the larvae, an unquenched fluorescent lipid was administered to 5 dpf larvae, and the appearance of labeled lipid in the pharynx and intestinal lumen before the gallbladder was noted (FIGS. 3C & 4). Second, that gallbladder fluorescence reflects hepatobiliary transport of the fluorescent cleavage products was shown by demonstrating the absence of PLA$_2$ activity in dissected adult gallbladders with and without bile (4785.+−.626 when full of bile vs. 7421.+−.2043 when empty, arbitrary fluorescence units ±.SEM, n=3). Dissected adult gall bladders were lysed in embryo medium (EM) (30 µl) containing BODIPY-FL-C$_5$-PC (0.1 µg) to release bile. PLA$_2$ activity was determined as described (1). Measurements were compared with activity of bile-depleted gallbladders. Third, this finding was confirmed by demonstrating the early appearance of fluorescent cleavage products in the liver of larvae exposed to PED6 compared with the gallbladder (FIG. 4). Larvae were labeled with PED6 (0.3 μg/ml) in EM, anesthetized (tricaine, 170 μg/ml), and placed in depression slides. Fluorescent images were captured over 1 hr using a Zeiss Axiocam 2 mounted on a Leica MZFL-III. Because $PLA_2$ activity was not detected in bile and fluorescent PED6 metabolites underwent rapid hepatobiliary transport, labeling the liver before the gall bladder, PED6 must be cleaved within the intestine.

Figure 5:
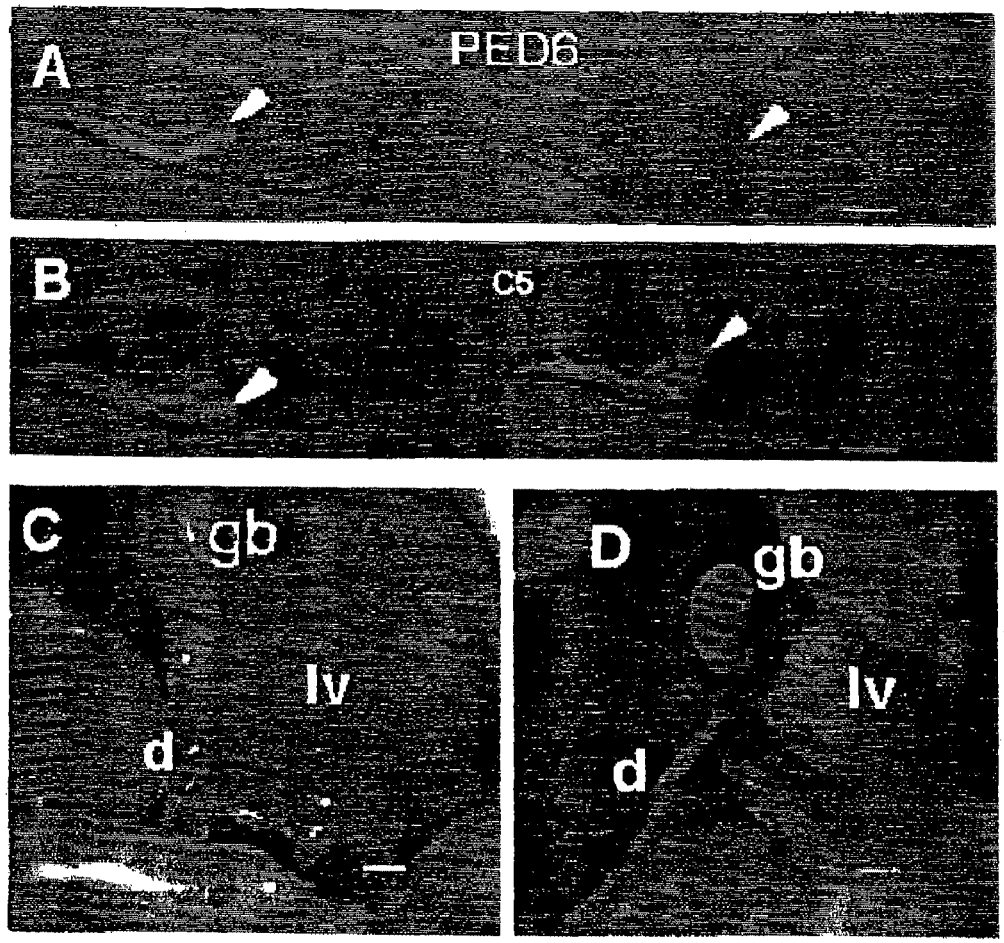
FIG. 5. Lipid processing. A. and B. Atorvastatin (ATR) inhibits processing of PED6 (A) but not of BODIPY-FL-C5 (Molecular Probes). B. Larvae were bathed in fluorophore (0.6 μM) in the presence or absence of atorvastatin (Lipitor tablet suspension containing 1 mg/ml) (arrowhead, gall bladder). C. Mouse digestive organs. D. Gall bladder fluorescence after processing (t=30 min) of PED6 (1 μg), administered by gavage. Symbols: gb, ball bladder; d, common bile duct; lv, liver. Scale bars, 1.0 mm (C and D), 200 μm (other images).

Moreover, PED6 labeling of the gall bladder was completely blocked by atorvastatin (Lipitor, Parke-Davis) (FIG. 5A), a potent inhibitor of cholesterol synthesis in humans (108). Because the addition of exogenous bile reversed this effect [Bile was obtained from freshly killed tilapia (Orechromis mossambicus) and extracted with three volumes of methanol:chloroform (1:2). The aqueous fraction was recovered, reduced to one volume under nitrogen, and added to EM (20 μl/ml)], and atorvastatin failed to inhibit processing of a water-soluble short-chain fatty acid (BODIPY-FL-C5, Molecular Probes Inc.) (105) (FIG. 5B), the data demonstrate that atorvastatin blocks the synthesis of cholesterol-derived biliary emulsifiers needed for dietary lipid absorption (109). These results, coupled with the rapid appearance of biliary fluorescence in mice fed PED6 (FIG. 5D), demonstrate that in zebrafish larvae, lipids are processed in a similar, if not identical, manner as other vertebrates and that gallbladder fluorescence reflects intestinal absorption and hepatic excretion of the lipid reagents and its metabolites.

BODIPY FR-PC a Reporter of Both Substrate and Cleavage Product

Figure 6:
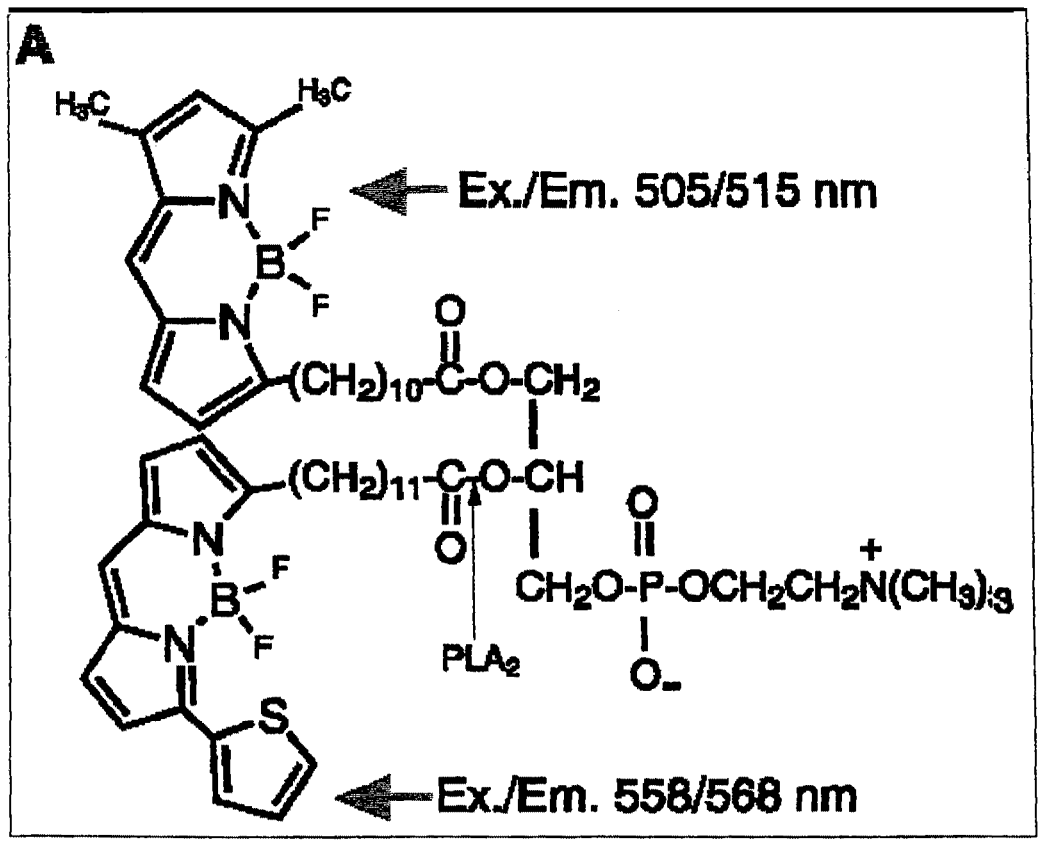
FIG. 6. BODIPY FR-PC reveals both the substrate and PLA$_2$ cleavage product. Upon integration into cells, excitation at 505 nm results in an emission at 568 nm (orange) due to fluorescence resonance energy transfer (FRET). After cleavage by PLA$_2$ emission is observed only at 515 nm (green).
Figure 7:
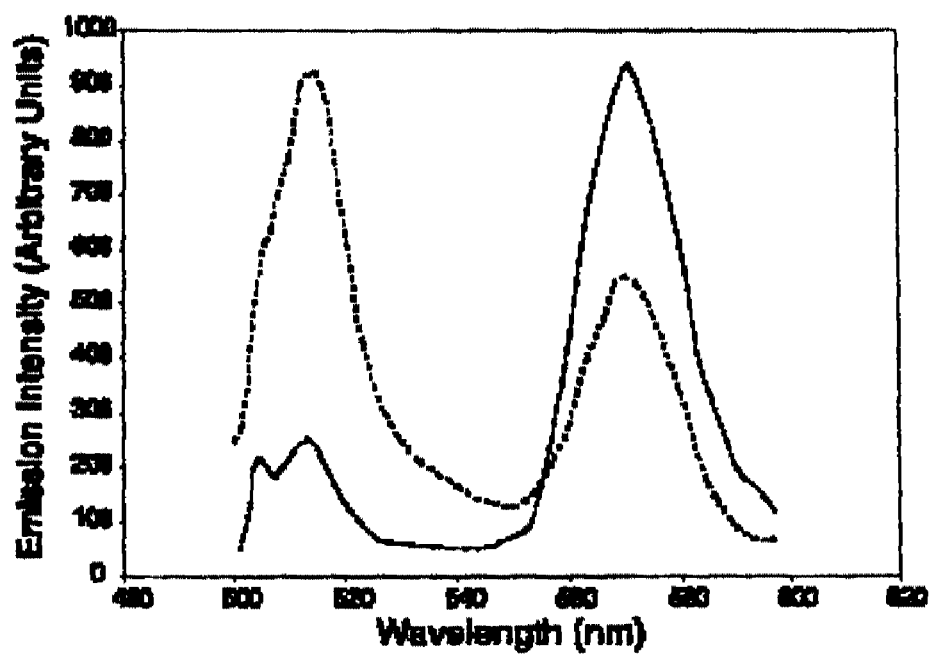
FIG. 7. Fluorescence emission spectrum of mixed micelles of 0.05 mol % BODIPY FR-PC in mixed-lipid vesicles. The fluorescence emission spectrum of BODIPY FR-PC (0.5 μM in ethanol; excitation, 505 nm) showed peaks at 514 nm and 568 nm with a ratio of 1.0 indicating FRET. An excitation scan (emission, 568 nm) showed peaks at 507 and 560 nm with a ratio (507/560) of 1.2. Solid line: before addition of PLA$_2$. Dashed line: after addition of N naja PLA$_2$. Vesicles were prepared by sonication of the dried lipids (from chloroform-methanol solution); 1.1 μM BODIPY FR-PC (0.05 mol %), 0.1 mM dimyristoylphosphatidycholine (46 mol %), 0.12 mM ditetradecylphospha-tidylmethanol (54 mol %), buffer (50 mM Tris, pH 8, 100 mM NaCl, 1 mM CaCl$_2$); excitation, 505 nm.

To further demonstrate that PED6 and other fluorescent lipids are processed by intestinal lipases prior to transport to the liver and gallbladder (as compared to being absorbed from the intestinal lumen, transported to the liver, and first cleaved by hepatic $PLA_2$ activity prior to biliary excretion) a new fluorescent lipid was developed (FIG. 6). BODIPY FR-PC (FIG. 6) is a substrate that can be used to determine the site of $PLA_2$ activity more precisely because it emits distinct fluorescent profiles before and after cleavage. This phospholipid contains two dyes that interact via fluorescence resonance energy transfer (FRET). Substrate and cleavage product possess unique spectral signatures, allowing their tissue distribution to be distinguished by fluorescence microscopy. Excitation (505 nm) of micelle-incorporated BODIPY FR-PC produces an orange emission (568 nm) (FIG. 7) from the sn2 fluorophore via the FRET effect (18). Cleavage of the substrate purified by $PLA_2$, however, releases the sn2 acyl chain and abolishes FRET (FIG. 7). Excitation of the resultant lysolipid produces a green emission (515 nm). The fluorescence emission spectrum of BODIPY FR-PC was determined using mixed micelles of 0.05 mol % BODIPY FR-PC in dimyristoyl phosphatidylcholine (46 mol %) and ditetradecylphosphatidylmethanol (54 mol %) prepared in buffer (50 mM Tris, pH 8, 100 mM NaCl, 1 mM $CaCl_2$) by sonication of the dried lipids.

Figure 8:
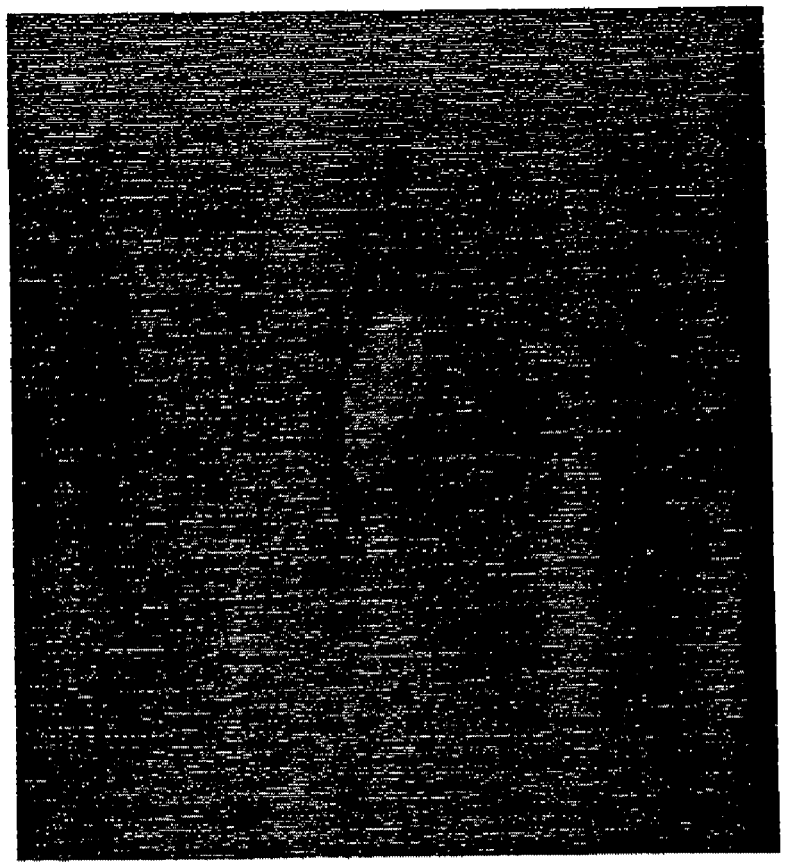
FIG. 8. BODIPY FR-PC is effective in paramecium. Paramecium incubated (1 hr) in BODIPY FR-PC (2.5 μg/ml) results in labeling of lipid droplets (orange). Digestion of the lipid results in green fluorescence. Excitation 505 nm, emission LP520.

Having established that BODIPY FR-PC behaves as anticipated in in vitro assays, its behavior in vivo was analyzed by exposing paramecia to the lipid for 1 hr, followed by excitation at 505 nm. As expected, FRET emission (orange) was observed from lipid droplets within individual paramecium soon after exposure, followed by the gradual appearance of BODIPY emission at 515 nm (green fluorescence) indicative of substrate cleavage (FIG. 8).

Figure 9:
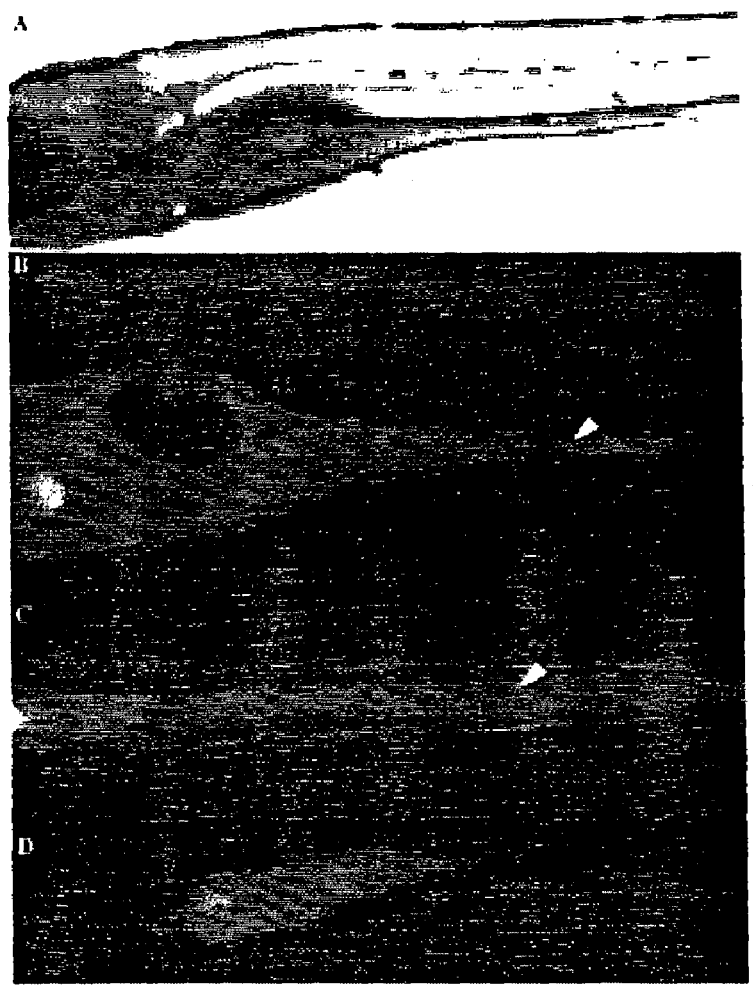
FIG. 9. BODIPY FR-PC localizes to the intestinal epithelium. Fish were incubated (1-4 hr) in BODIPY FR-PC (2.5 μg/ml). BODIPY FR-PC metabolites are observed in gall bladder (green). Excitation 505 nm, mission LP520. A. Brightfield image. B. and C. Visualization of antigen presenting enterocytes in segment II of the larval zebrafish intestine after only 1 hr of labeling. Arrows mark segment II domain. D. 4 hr labeling with BODIPY FR-PC results in FRET effect throughout intestine.

To further demonstrate the behavior of BODIPY FR-PC in vivo, 5 dpf zebrafish larvae were bathed in BODIPY FR-PC. Within 1 hr, larvae exposed to BODIPY FR-PC showed a bright green fluorescent gallbladder and orange fluorescence within the apical cytoplasm of posterior intestinal cells (FIG. 9C). These cells are known to absorb luminal macromolecules through pinocytosis (107). Orange fluorescence indicative of uncleaved substrate also was observed after 4 hr of incubation in the anterior intestine epithelium, the site of lipid absorption in fish (82, 95). FRET emission was never detected in the liver even after prolonged incubation (FIG. 9D), implying that gallbladder fluorescence following ingestion of labeled lipids is due to cleavage by intestinal $PLA_2$s.

The evidence of the instant invention is consistent with the predicted pathway of lipid processing observed in mammals since uncleaved substrate (orange) was seen only in the intestinal epithelium. Over time, continuous exposure to BODIPY FR-PC either overwhelms intestinal lipase activity or leads to the integration of BODIPY FR-PC into the cellular phospholipid pool. Regardless, the data of the present invention provide further evidence that in zebrafish, as in mammals, lipids are absorbed and modified in the intestine prior to transport to the liver.

Lipid Processing in Zebrafish Intestinal Mutants

Figure 10:
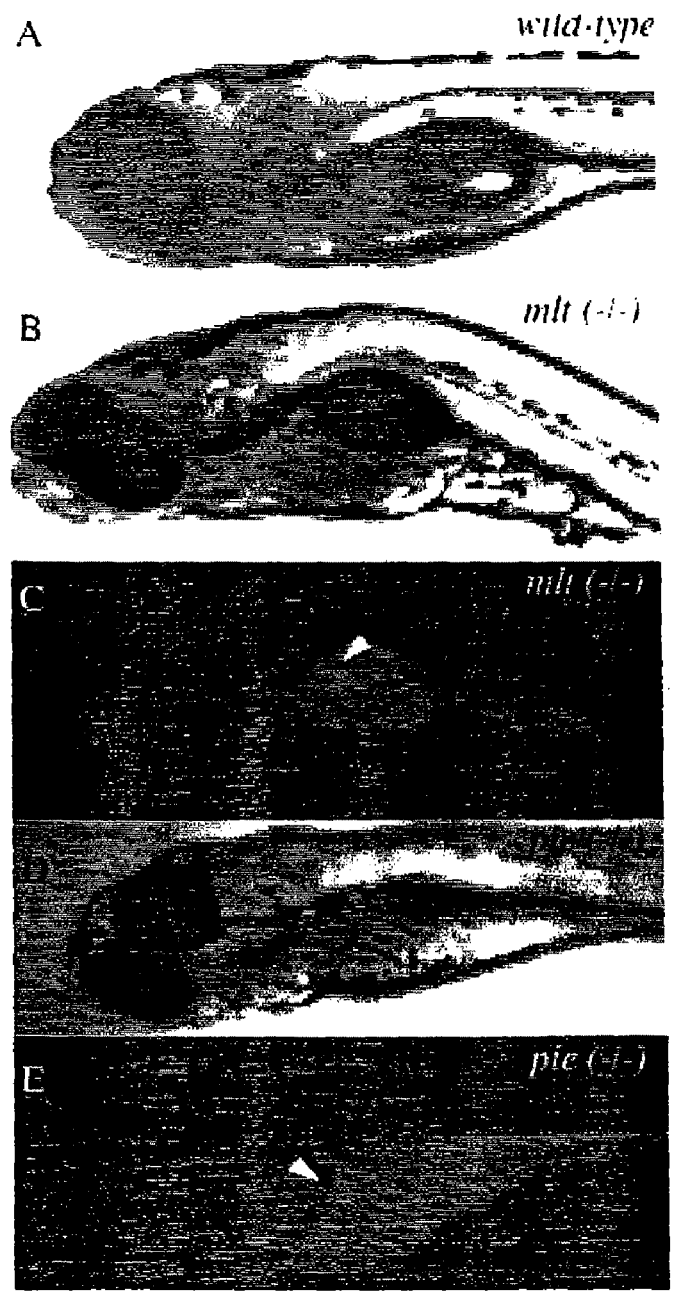
FIG. 10. Lipid processing in intestinal mutants. A and C. Bright field images of 5 dpf mlt and pie larvae. B and D. Fluorescent images corresponding to A and C. Normal lipid processing of PED6 (0.3 μg/ml, 2 hr) in mlt larva (arrowhead marks gallbladder). D and E. Abnormal lipid processing in PED6 labeled pie and slj larvae; fluorescence is present in the intestinal lumen (white arrowhead) and reduced in the gallbladder (red arrowhead).

To determine the utility of the fluorescent lipids as reagents in a genetic screen, PED6 was administered to mutants known to perturb intestinal morphology (31), and the pattern and timing of gallbladder fluorescence was examined (FIG. 10). These mutations cause embryonic lethality and each of the affected genes regulate intestinal development in a region-specific manner. The mutations slim jim (slj) and piebald (pie) each cause degeneration of anterior intestinal epithelium and exocrine pancreas, whereas meltdown (mlt) results in cystic expansion of the posterior intestine. As shown in FIGS. 10B and 10C, mlt mutants retain PED6 processing in the anterior intestine and show normal levels of gall bladder fluorescence. In contrast, pie (FIGS. 10D & 10E) and slj (FIG. 10F) mutants display greatly reduced gall bladder labeling. Although slj and pie have similar histological phenotypes, gall bladder fluorescence was absent in pie larvae but visible in slj larvae, albeit at a reduced level compared with wild-type or mlt larvae (FIGS. 10B & 10C). Hence, fluorescent lipids can be used to identify mutants with abnormal digestive organ morphology.

Screening for Mutations that Perturb Lipid Processing Using Fluorescent PLA 2 Substrates Lipid reporters also are effective tools for identifying mutations that perturb lipid metabolism without causing obvious morphological defects. In a pilot screen, larval progeny of individual F2 families derived from an ENU mutagenesis protocol were bathed in PED6 and screened for digestive organ morphology and phospholipid processing. PED6 fluorescent metabolites dramatically enhanced digestive organ structure, facilitating scoring of gallbladder development, intestinal folding, and bile duct morphology. From 190 genomes screened, two mutations were identified and confirmed in the subsequent generation. These mutations were recovered based on their pattern of gallbladder fluorescence, not morphological criteria, thereby supporting the use of the fluorescent lipids of the instant invention in large-scale mutagenesis screens.

Lipid processing was examined further in the identified mutants using a fluorescent cholesterol analog (FIG. 1).

EXAMPLE 1

Characterize the Biochemical Pathways Responsible for the Metabolism of the Fluorescent PLA$_2$ Substrates in Zebrafish To characterize, biochemically, the identity of fluorescent compounds present in the bile of zebrafish following exposure to fluorescent PLA$_2$ substrates and other lipid molecules, zebrafish were exposed to a panel of fluorescent phospholipids and free fatty acids that differed in acyl chain length and fluorophore position. The experiments enabled the determination of the phenotypic significance of recovered mutants by identifying shared pathways of lipid metabolism in zebrafish and mammals.

Identity of the Fluorescent Lipid in the Bile of Fish Labeled with PED6

To determine whether the fluorescence in the bile is due to a reacylated phospholipid (lacks the DNP quencher on the head group) or exists as a free BODIPY-labeled fatty acid, adult fish were labeled with PED6 by gavage. Adult fish were used because of the small amount of lipid in larvae bile. Under a fluorescence stereomicroscope, the gall bladders were easily identified by their intense fluorescence. The gall bladders were removed at various times post-gavage and placed in cold methanol, sonicated and extracted (97).

Figure 11:
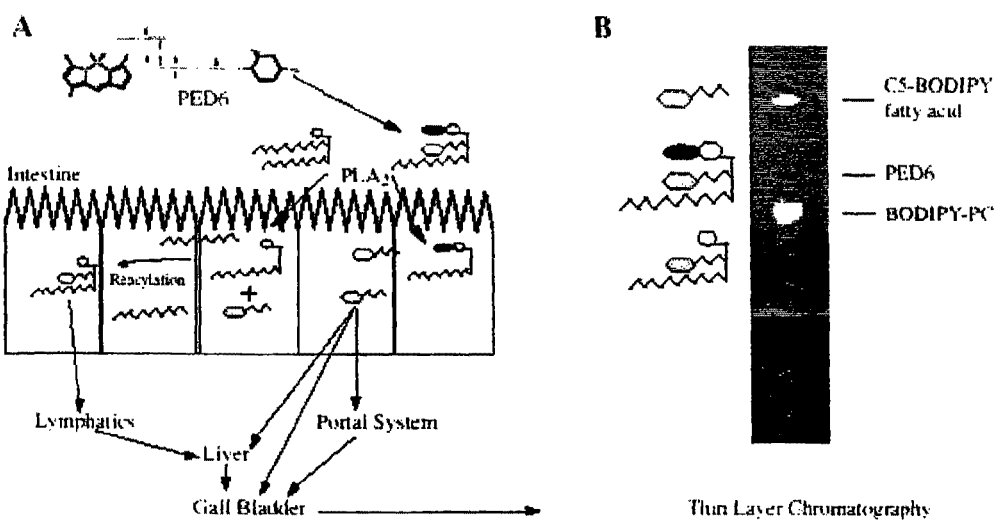
FIG. 11. Phospholipid processing and transport. A. Following uptake, PED6 is cleaved by PLA$_2$ liberating a labeled fatty acid. The fate and transport of this fatty acid remains unknown. B. TLC of fluorescent lipid standards. PED6 (black because it is quenched), D3803 (C5-BODIPY PC), and C5-fatty acid are easily resolved using a two solvent system silica gel plates (Whatman, LK5D). Solvent 1 (toluene, ether, ethanol, acetic acid; 25/15/2/0.2); Solvent 2 (chloroform, methanol, acetic acid, water; 25/15/4/2).
Figure 12:
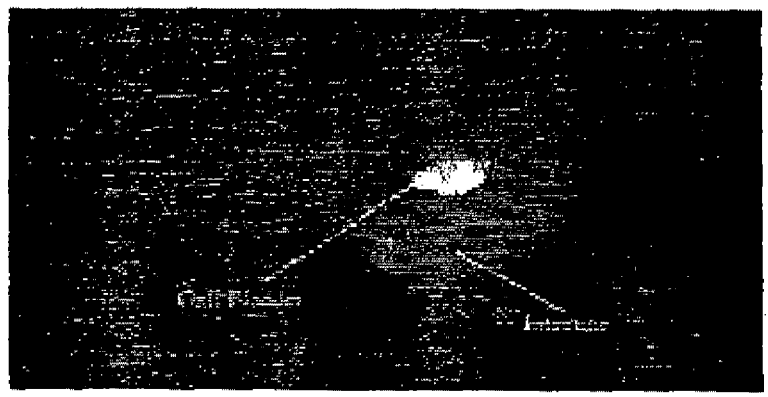
FIG. 12. Red BODIPY-PC given by gavage labels the gall bladder. Adult fish was anesthetized in tricaine, injected with 80 μg of D3806 (a BODIPY PC 582/593 nm), allowed to recover for 1 hr and dissected on ice.

The organic fraction was then subjected to TLC analysis as described to determine whether the fluorescent sn2 acyl chain was re-esterified prior to biliary excretion (FIGS. 11A & 11B) (36, 98). This procedure was performed on five fish using D3806 (a red BODIPY PC, 582/593) (FIG. 12).

Identity of the Fluorescent Lipids in the Bile of Fish Labeled with BODIPY-C5. C12, C16 Fatty Acids To ascertain whether short chain fatty acids are transported via the portal system, adult zebrafish are injected with C16, C12 and C5 BODIPY-labeled fatty acids and then the fluorescent bile characterized biochemically using TLC. Based on work in other vertebrates, only short-chain fluorescent fatty acids can pass directly into the bile, consistent with transport via the portal vein, following injection of C16 BODIPY fatty acid (82, 99). The profile and kinetics of labeling are very different with the shorter chain analogues.

Labeling of 5 dpf Larvae with BODIPY Labeled Fatty Acids and Phospholipids

To extend the findings from the adult bile assays to younger fish, the rate of gallbladder fluorescence in zebrafish larvae exposed to BODIPY-labeled fatty acids and phospholipids with different chain lengths is compared. Larvae are soaked in the identical BODIPY fatty acids injected into the adults, and the rate of gall bladder fluorescence is assayed. The labeling rate is determined by placing a fish in water containing the fluorescent substrate and capturing a digital image of a lateral view (Axiovision, Zeiss and ImageQuant, Molecular Dynamics Inc.). The gall bladder fluorescence is quantified at various time intervals to compute the rate of change over time. Delayed appearance of gallbladder fluorescence after exposure to long chain fatty acids and phospholipids lends further support to the hypothesis that acyl chain length plays a role in lipid transport in zebrafish.

PLAN Isoform Mediation of PED6 Processing

It is well established that cPLA$_2$ and some iPLA$_2$ isoforms exhibit acyl chain specificity and favor phospholipids that contain arachidonic acid, the precursor of eicosanoids (41, 44). Despite the fact that the fluorescent phospholipids do not contain arachidonic acid, the placement of the BODIPY moiety on the sn2 position results in significant cleavage by cPLA$_2$ (36, 94). The ability of the BODIPY moiety to disrupt the membrane and its hydrophobicity are both properties similar to arachidonic acid that enable cleavage by cPLA$_2$ (100). Secreted PLA$_2$ isoforms exhibit no acyl chain specificity (34). Fluorescent phospholipids that contain a saturated acyl chain on the sn2 position are fine sPLA$_2$ substrates but poor cPLA$_2$ ones.

To identify which PLA$_2$ isoforms mediate the appearance of fluorescence in the gall bladder, the rate of gall bladder fluorescence is compared in larvae exposed to two types of substrates. Larvae are labeled with two phospholipid substrates that differ in their specificity for cPLA$_2$: a PL with an sn1 BODIPY and an sn2 saturated acyl chain—a poor PLA$_2$ substrate, or BODIPY FR-PC—a good cPLA$_2$ substrate. If little difference is observed in the rates of gall bladder fluorescence using the two substrates, then the critical lipase important for the processing of these lipids is a secreted PLA$_2$ isoform, a promiscuous enzyme that exhibits little acyl chain preference (96). BODIPY FR-PC is used because no other available fluorescent phospholipid contains sn2 arachidonic acid.

Taken together, the experiments clarify the relevant PLA$_2$ isoforms, the route(s) of phospholipid/fatty acid transport, and allow refinement of the screening reagents (e.g., by preparing cocktails of fluorophores to target specific transport processes).

EXAMPLE 2

A Mutagenesis Screen to Identify Genes that Regulate Lipid Processing in Zebrafish In the instant invention a large-scale genetic screen for genes that regulate lipid processing in zebrafish using fluorescent PLA$_2$ substrates is disclosed. This screen leads to the recovery of mutations that regulate a wide range of developmental and physiological processes. As outlined, the screen identifies mutations that either resemble or are allelic to previously described intestinal mutations. Given the large number of steps required for processing of the fluorescent PLA$_2$ substrates, however, this screen leads to the recovery of genes that could not be identified using standard screening strategies. These include, but are not limited to, genes that directly regulate PLA$_2$; genes responsible for the development of the liver, biliary system, and the intestinal vasculature and lymphatics; and genes that play a direct role in lipid metabolism and transport.

Figure 13:
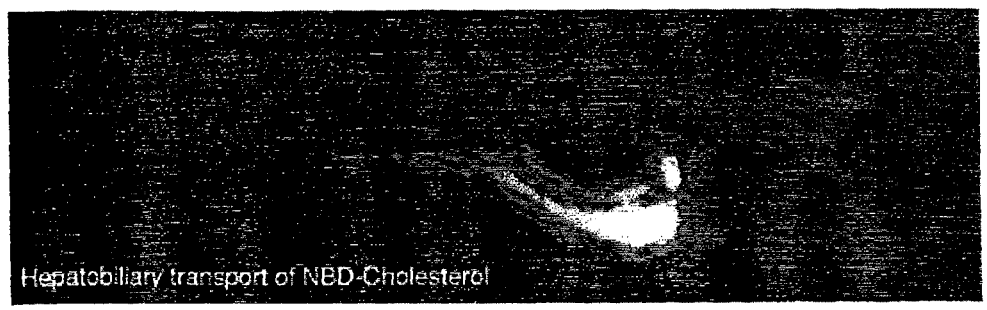
FIG. 13. Larval zebrafish (5 dpf) labeled with NDB cholesterol—derivative labels gall bladder within 30 minutes of ingestion (3 μg/ml, solubilized with fish bile).

The mutagenesis and screening strategies of the instant invention incorporate several well established methodologies. First, adult male fish are mutagenized with ENU using established dosing schedules. Second, the F1 progeny of the mutagenized G0 fish will be bred to homozygosity using a classical 3 generation protocol (F3 screen), as well as parthenogenetically, using the early-pressure (EP) technique (103). Zebrafish larvae generated in this fashion are soaked in the BODIPY FR-PC, PED6, and/or NBD cholesterol (FIG. 13) lipid reagents at 5 dpf and then screened for defects in lipid processing based upon the timing and pattern of fluorescence in the intestine, liver and gallbladder. Parallel F3 and EP screens are employed because they offer the best opportunity to maximize the use of resources. Although EP screens are in many ways less efficient than classical F3 screens, they are suited to moderate sized fish facilities and require less manpower because of the reduced number of matings required.

ENU Mutagenesis

For the EP screen, adult male fish from the "*AB" zebrafish line (this line of fish carries the fewest number of haplo-insufficient or lethal mutations of common lab strains)

are exposed to ENU (3.5 mM) in a secluded fume hood for 30 minutes on 3 consecutive days. After taking the necessary precautions to remove adherent ENU, the fish are returned to the main fish facility and outcrossed to WT fish from the Wik genetic background 3 weeks after mutagenesis, and the F1 progeny are raised to sexual maturity. To improve the likelihood that the *AB mutagenized males do not carry significant mutations in their genetic background, mutagenized males are outcrossed only if 5 of their female siblings produce large clutches of viable EP embryos that survive to 5 dpf. The efficacy of ENU mutagenesis is determined prior to outcrossing by calculating the specific locus rate for new mutations at the alb, spa, and bra loci.

One week after ENU exposure, the mutagenized G0 males are mated to double-mutant "tester" female carriers of the alb, spa, and bra mutations and their 32 hpf progeny are analyzed for clones of alb/alb, spa/spa, and bra/bra mutant pigmented cells. Based upon published SLR's for these loci using our ENU dosing schedule there is a need to analyze approximately 1500-2000 progeny from each mutagenized G0 fish to accurately determine the efficacy of mutagenesis.

Screening for Mutations that Perturb Lipid Processing

For screening, 5 dpf larvae derived from pair-wise matings of F2 families or EP treatment of F1 females are soaked fluorescent lipids for 1-10 hrs and analyzed for perturbation of lipid processing using a fluorescent stereo-microscope (Leica MZ FLIII). The BODIPY FR-PC and PED6 reagents used in the screen are purified via TLC, resuspended in ethanol/DMSO and tested in vivo using WT 5 dpf larvae prior to screening. The F3 5 dpf larvae for screening are derived from pair-wise matings of fish from F2 families, while 5 dpf larvae produced parthenogenetically are produced using standard EP protocols: briefly, eggs are collected from anesthetized F1 females (tricaine) and exposed to UV irradiated sperm following standard in vitro fertilization (IVF) protocols. Immediately after IVF (1.4 min.), the fertilized eggs are exposed to 13,000 psi in a French Press for 4-6 min, then slowly returned to ambient atmospheric pressure and allowed to develop until 5 dpf (103).

Putative mutations that alter the pattern or rate of accumulation of lipid fluorescence in the digestive organs, as well as those that produce specific alterations in larval morphology, are recovered and outcrossed for future analysis. Mutations that result in a generalized delay in larval development are not analyzed given their high frequency of recovery in prior chemical mutagenesis screens. For the F3 screen, no less than 20, 5 dpf larvae are analyzed from ≧6 crosses per F2 family. Using this strategy, excluding lethal effects of haploinsufficiency in heavily mutagenized genomes, the theoretical chance of recovering a mutation present in the genome of an F2 family is ≧89%. For the EP screen, all of the viable progeny derived from each F1 female are analyzed. In contrast to the F3 screen, the statistical likelihood of recovering mutations in the genome of F1 females treated with EP is not predictable given the tendency to recover smaller viable clutches with this technique, and the potential for meiotic recombination to alter Mendelian inheritance patterns. Only those heritable defects that can be recovered in statistically significant Mendelian ratios when outcrossed, are considered mutations.

The data and analysis of known intestinal mutants suggest that lipid processing mutations are not rare mutations. A total of approximately 750-2000 mutanized genomes are screened.

EXAMPLE 3

Determination of the Physiological Significance and Molecular Nature of Recovered Mutations The instant invention discloses methods for characterizing, both phenotypically and molecularly, the generated mutations. Phenotypic analysis is approached first. Mutations that affect a wide range of developmental and physiological processes are recovered in the screen. Careful phenotypic analysis of these mutants is important for several reasons. First, it allows quantitation of the range and frequency of phenotypes actually recovered using the fluorescent lipid reagents. Second, it allows the performance of comprehensive complementation analyses so that hypomorphic alleles of interesting mutations are not overlooked. Third, it allow the selection of those mutations worthy of molecular analysis now versus mutations that may be of more immediate interest to other members of the zebrafish scientific community. The rationale for the molecular analysis of zebrafish mutations is well known to those of skill in the art. Recognition of the importance of phenotypic analyses of mutant phenotypes prior to molecular analyses is relevant given the large amount of work that is often required to identify the responsible gene.

Phenotypic Analyses

Mutant phenotypes recovered using the screen of the instant invention can be categorized into several broad categories. First, using morphological and histological criteria mutations that visibly perturb structural development of the pharynx, esophagus, intestine, liver and biliary tract are distinguished from those mutants that appear normal. The latter group is considered physiological mutants and is categorized based upon its handling of the panel of fluorescent lipids of the instant invention. This group encompasses, but is not limited to, mutations affecting the intestinal epithelium, liver, vasculature and lymphatics, enteric neuromusculature, and the tissue specific regulation of $PLA_2$.

Embryological and transient expression assays also are important studies that can aid phenotypic analyses of zebrafish mutants. Unfortunately, mutations affecting development of the zebrafish digestive organs are, in general, less easily analyzed using these techniques than mutations affecting early development. The short half-life of injected RNA transcripts and DNA expression constructs coupled with the mosaic distribution of the micro-injected DNA limits the utility of transient expression assays for mutations that are not recognizable until 4-5 dpf.

In one embodiment of the instant invention, histological analyses are performed by fixing larvae in 4% paraformaldehyde, embedding the fixed larvae in glycolmethacrylate, and followed by sectioning. Sections are stained using toluene blue/azure II as described and analyzed using a Zeiss Axioplan compound microscope. When needed, selected immunocytochemical and molecular markers are employed to further categorize organ specific defects. If necessary ultrastructural studies are performed as well. For "physiological" mutations, affected larvae are sequentially soaked in the fluorescent lipids of the instant invention, thereby allowing a more detailed categorization.

Molecular Analyses

The molecular characterization of zebrafish mutations can be performed using techniques widely known to those of skill in the art. These techniques include, but are not limited to, use of an ever expanding array of physical and genetic markers, several large insert genomic DNA libraries, outstanding bioinformatics, and a successful EST program.

Recent announcement of plans to physically map and sequence the zebrafish genome suggest that within 2-3 years molecular characterization of zebrafish mutants will be greatly simplified. One of the major advantages of working in zebrafish compared with other vertebrates is the potential to generate high-resolution maps of mutant loci. Since mutations can be confidently mapped to within 0.1 cM, the critical interval surrounding a mutant locus can be narrowed to include relatively few candidate genes. The recent identification of the genes responsible for several zebrafish mutants demonstrates this nicely.

In one embodiment of the instant invention, the molecular characterization of identified mutations is accomplished by introducing mutations into a polymorphic genetic background and assigning a chromosomal location using either bulk segregant analyses and polymorphic markers from the 25 zebrafish linkage groups or using half tetrads and polymorphic centromeric markers. Concomitantly, DNA from large numbers of mutant progeny from the "map cross" are extracted and stored. Thereafter, the genetic map of the region surrounding the locus is refined using standard PCR based techniques and genetic markers from existing maps.

The closest known genetic markers flanking the mutant locus are then used to screen large insert genomic libraries to identify more closely linked markers. For BAC and PAC clones this involves direct sequencing, whereas for YAC clones this requires rescue and sequencing of the zebrafish genomic DNA adjacent to the YAC arms. Ultimately, flanking markers within 0.1 cM of the mutant locus are identified, and a BAC or PAC clone spanning the locus is analyzed for the responsible gene. The latter is accomplished by direct sequencing, using the genomic insert to probe an appropriately staged genomic library and/or exon trapping. Confirmation of mutation is accomplished via expression analyses and mutant rescue, using transient analyses, if possible, or via transgenesis. Identification of tightly linked flanking markers generally involves a BAC, PAC, or YAC chromosomal walk, using markers mapped genetically and physically (radiation hybrid panel).

In one embodiment of the instant invention, genetic mapping is performed using PCR based techniques. SSR polymorphisms are resolved using denaturing (SSR) polyacrylamide gel electrophoresis while single base-pair polymorphisms are resolved using Conformation Sensitive. Gel Electrophoresis (CSGE), a non-denaturing technique related to SSCP. DNA detection is accomplished using a Molecular Dynamics Fluorescent Scanner; PCRs use Cy-5 end-labeled primers. PCR fragments generated using non-fluorescent primers are visualized on polyacrylamide gels after staining with the fluorescent intercalating dye Syto-61 (Molecular Probes). For bulk segregant analyses, separate pools of DNA from 25 mutant larvae and 25 sibling WT larvae are generated and the segregation of SSR or single base pair polymorphic markers derived from ESTs analyzed.

For physical mapping, the LN 540 (104) and Goodfellow Radiation Hybrid panels are employed. Markers are mapped using a PCR based strategy and computer assisted analysis of amplification patterns. Screening of genomic libraries, rescue of YAC ends, generation of YAC, BAC, and PAC clones is accomplished using the commercial suppliers or published protocols, which are known to those of skill in the art. All other molecular techniques outlined above employ published protocols, which also are known to those of ordinary skill in the art.

EXAMPLE 4

Drug Screening Assays

The invention provides methods for identifying compounds or agents that can be used to treat disorders characterized by (or associated with) aberrant or abnormal lipid and/or cholesterol metabolism. These methods are also referred to herein as drug screening assays and typically include the step of screening a candidate/test compound or agent for the ability to modulate (e.g., stimulate or inhibit) lipid and/or cholesterol metabolism. Candidate/test compounds or agents that have one or more of these abilities can be used as drugs to treat disorders characterized by aberrant or abnormal lipid and/or cholesterol metabolism. Candidate/test compounds or agents include, for example, (1) peptides such as soluble peptides, including Ig-tailed fusion peptides and members of random peptide libraries (see e.g., Lam, K. S. et al. (1991) Nature 354:82-84; Houghten, R. et al. (1991) Nature 354:84-86) and combinatorial chemistry-derived molecular libraries made of D- and/or L-configuration amino acids; (2) phosphopeptides (e.g., members of random and partially degenerate, directed phosphopeptide libraries, see, e.g., Songyang, Z. et al. (1993) Cell 72:767-778); (3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and (4) small-organic and inorganic molecules (e.g., molecules obtained from combinatorial and natural product libraries).

In one embodiment, the invention provides a method for identifying a compound capable of use in the treatment of a disorder characterized by (or associated with) aberrant or abnormal lipid and/or cholesterol metabolism. This method typically includes the step of assaying the ability of the compound or agent to modulate lipid and/or cholesterol metabolism, thereby identifying a compound for treating a disorder characterized by aberrant or abnormal lipid and/or cholesterol metabolism. Disorders characterized by aberrant or abnormal lipid and/or cholesterol metabolism are described herein. The invention provides screening assays to identify candidate/test compounds or agents that modulate lipid and/or cholesterol metabolism. Typically, the assays include the steps of identifying at least one phenotypic perturbation of lipid and/or cholesterol metabolism in an organism, administering at least one quenched or fluorescently-tagged phospholipid, cholesterol or other lipid analogue to the organism having the phenotypic perturbation, administering a candidate/test compound or agent to the organism under conditions that allow for the uptake of the candidate/test compound or agent by the organism and wherein but for the presence of the candidate/test compound or agent the pattern of fluorescence would be unchanged, and detecting a change in the pattern of fluorescence by comparing the pattern of fluorescence prior to candidate/test compound or agent administration with that seen following administration of the candidate/test compound or agent.

Mutagenesis screens using fluorescent lipids exploit the advantages of combining genetic analyses with imagining of enzymatic function. The existence of related lipid processing mechanisms in mammals and teleosts, and the finding that therapeutic drugs used to modify lipid metabolism in humans are active in zebrafish, establish that genetic screens can be designed to probe the mechanistic basis of acquired and heritable human disorders. The evidence of the instant invention demonstrates that lipid metabolism in mammals and fish can be monitored with fluorescent lipids, and that such organisms metabolize ingested fluorescent lipids in an analogous manner. Consequently, the methods for using the fluorescent lipids of the instant invention to study lipid metabolism, identify diseases of lipid metabolism, and/or to identify agents to treat therapeutically or prophylatically diseases or disorders of lipid metabolism and genetic screening are applicable to all vertebrate model organisms, including, but not limited to, rodents, amphibia, and fish. Fluorescent reporters are predicted to identify genes, including but not limited to, genes involved in diseases of lipid metabolism, such as atherosclerosis; in disorders of biliary secretion, such as biliary atresia; and in cancer, a disease in which lipid signaling plays an important role. Identification of these genes has important implications for cancer research and research related to diseases of the liver, intestine and cardiovascular system.

While this invention has been described with a reference to specific embodiments, it will be obvious to those of ordinary skill in the art that variations in these methods and compositions may be used and that it is intended that the invention may be practiced otherwise than as specifically described herein. Accordingly, this invention includes all modifications encompassed within the spirit and scope of the invention as defined by the claims.

REFERENCES

1. Nusslein-Volhard, C. (1994) Of flies and fishes. *Science* 266, 572-574.
2. Driever, W., Solnica-Krezel, L., Schier, A. F., Neuhauss, S. C., Malicki, J., Stemple, D. L., Stainier, D. Y., Zwartkruis, F., Abdelilah, S., Rangini, Z., Belak, J., and Boggs, C. (1996) A genetic screen for mutations affecting embryogenesis in zebrafish. *Development* 123, 37-46.
3. Haffter, P., Granato, M., Brand, M., Mullins, M. C., Hammerschmidt, M., Kane, D. A., Odenthal, J., van Eeden, F. J., Jiang, Y. J., Heisenberg, C. P., Kelsh, R. N., Furutani-Seiki, M., Vogelsang, E., Beuchle, D., Schach, U., Fabian, C., and Nusslein-Volhard, C. (1996) The identification of genes with unique and essential functions in the development of the zebrafish, Danio rerio. *Development* 123, 1-36.
4. Brownlie, A., Donovan, A., Pratt, S. J., Paw, B. H., Oates, A. C., Brugnara, C., Witkowska, H. E., Sassa, S., and Zon, L. I. (1998) Positional cloning of the zebrafish sauternes gene: a model for congenital sideroblastic anaemia [see comments]. Nature Genetics 20, 244-250.
5. Chandrasekhar, A., Schauerte, H. E., Haffter, P., and Kuwada, J. Y. (1999) The zebrafish detour gene is essential for cranial but not spinal motor neuron induction. *Development* 126, 2727-2737.
6. Fisher, S., and Halpern, M. E. (1999) Patterning the zebrafish axial skeleton requires early chordin function [see comments]. *Nature Genetics* 23, 442-446.
7. Halpern, M. E., Ho, R. K., Walker, C., and Kimmel, C. B. (1993) Induction of muscle pioneers and floor plate is distinguished by the zebrafish no tail mutation. *Cell* 75, 99-111.
8. Hashimoto, H., Itoh, M., Yamanaka, Y., Yamashita, S., Shimizu, T., Solnica-Krezel, L., Hibi, M., and Hirano, T. (2000) Zebrafish Dkk1 functions in forebrain specification and axial mesendoderm formation. *Developmental Biology* (Orlando) 217, 138-152.
9. Gritsman, K., Zhang, J., Cheng, S., Heckscher, E., Talbot, W. S., and Schier, A. F. (1999) The EGF-CFC protein one-eyed pinhead is essential for nodal signaling. *Cell* 97, 121-132.
10. Koos, D. S., and Ho, R. K. (1999) The nieuwkoid/dharma homeobox gene is essential for bmp2b repression in the zebrafish pregastrula. *Developmental Biology* (Orlando) 215, 190-207.
11. Parker, L., and Stainier, D. Y. (1999) The zebrafish diwanka gene controls an early step of motor growth cone migration. *Development* 126, 3461-3472.
12. Pelegri, F., Knaut, H., Maischein, H. M., Schulte-Merker, S., and Nusslein-Volhard, C. (1999) A mutation in the zebrafish maternal-effect gene nebel affects furrow formation and vasa RNA localization. *Current Biology* 9, 1431-1440.
13. Sampath, K., Rubinstein, A. L., Cheng, A. M., Liang, J. O., Fekany, K., Solnica-Krezel, L., Korzh, V., Halpern, M. E., and Wright, C. V. (1998) Induction of the zebrafish ventral brain and floorplate requires cyclops/nodal signalling. *Nature* 395, 185-189.
14. Zeller, J., and Granato, M. (1999) The zebrafish diwanka gene controls an early step of motor growth cone migration. *Development* 126, 3461-3472.
15. Zhong, T. P., Rosenberg, M., Mohideen, M. A., Weinstein, B., and Fishman, M. C. (2000) gridlock, an HLH gene required for assembly of the aorta in zebrafish. *Science* 287, 1820-1824.
16. Griffin, K. J., Amacher, S. L., Kimmel, C. B., and Kimelman, D. (1998) Molecular identification of spadetail: regulation of zebrafish trunk and tail mesoderm formation by T-box genes. *Development* 125, 3379-3388.
17. Woo, K., and Fraser, S. E. (1997) Specification of the zebrafish nervous system by nonaxial signals. *Science* 277, 254-257.
18. Furthauer, M., Thisse, C., and Thisse, B. (1997) A role for FGF-8 in the dorsoventral patterning of the zebrafish gastrula. *Development* 124, 4253-4264.
19. Feldman, B., Gates, M. A., Egan, E. S., Dougan, S. T., Rennebeck, G., Sirotkin, H. I., Schier, A. F., and Talbot, W. S. (1998) Zebrafish organizer development and germ-layer formation require nodal-related signals [see comments]. *Nature* 395, 181-185.
20. Nasevicius, A., Hyatt, T., Kim, H., Guttman, J., Walsh, E., Sumanas, S., Wang, Y., and Ekker, S. C. (1998) Evidence for a frizzled-mediated wnt pathway required for zebrafish dorsal mesoderm formation. *Development* 125, 4283-4292.
21. Mullins, M. C. (1999) Embryonic axis formation in the zebrafish. *Methods in Cell Biology* 59, 159-178.
22. Connors, S. A., Trout, J., Ekker, M., and Mullins, M. C. (1999) The role of tolloid/mini fin in dorsoventral pattern formation of the zebrafish embryo. *Development* 126, 3119-3130.
23. Ober, E. A., and Schulte-Merker, S. (1999) Signals from the yolk cell induce mesoderm, neuroectoderm, the trunk organizer, and the notochord in zebrafish. *Developmental Biology* (Orlando) 215, 167-181.
24. Alexander, J., Rothenberg, M., Henry, G. L., and Stainier, D. Y. (1999) casanova plays an early and essential role in endoderm formation in zebrafish. *Developmental Biology* (Orlando) 215, 343-357.
25. Weidinger, G., Wolke, U., Koprunner, M., Klinger, M., and Raz, E. (1999) Identification of tissues and patterning events required for distinct steps in early migration of zebrafish primordial germ cells. *Development* 126, 5295-5307.
26. Thisse, B., Wright, C. V., and Thisse, C. (2000) Activin- and Nodal-related factors control antero-posterior patterning of the zebrafish embryo. *Nature* 403, 425-428.

27. Schmid, B., Furthauer, M., Connors, S. A., Trout, J., Thisse, B., Thisse, C., and Mullins, M. C. (2000) Equivalent genetic roles for bmp7/snailhouse and bmp2b/swirl in dorsoventral pattern formation. *Development* 127, 957-967.
28. Argenton, F., Zecchin, E., and Bortolussi, M. (1999) Early appearance of pancreatic hormone-expressing cells in the zebrafish embryo. *Mechanisms of Development* 87, 217-221.
29. Reifers, F., Walsh, E. C., Leger, S., Stainier, D. Y., and Brand, M. (2000) Induction and differentiation of the zebrafish heart requires fibroblast growth factor 8 (fgf8/acerebellar). *Development* 127, 225-235.
30. Reiter, J. F., Alexander, J., Rodaway, A., Yelon, D., Patient, R., Holder, N., and Stainier, D. Y. (1999) Gata5 is required for the development of the heart and endoderm in zebrafish. *Genes & Development* 13, 2983-2995.
31. Pack, M., Solnica-Krezel, L., Malicki, J., Neuhauss, S. C., Schier, A. F., Stemple, D. L., Driever, W., and Fishman, M. C. (1996) Mutations affecting development of zebrafish digestive organs. *Development* 123, 321-328.
32. Bomalaski, J. S., and Clark, M. A. (1993) Phospholipase A2 and arthritis. [Review]. *Arthritis Rheum* 36, 190-198.
33. Dennis, E. A. (1997) The growing phospholipase A2 superfamily of signal transduction enzymes. *Trends Biochem Sci*, 22, 1-2.
34. Gijon, M., and Leslie, C. (1997) Phospholipases A2. *Seminars in Cell & Developmental Biology* 8, 297-303.
35. Miyashita, A., Crystal, R. G., and Hay, J. G. (1995) Identification of a 27 bp 5'-flanking region element responsible for the low level constitutive expression of the human cytosolic phospholipase A2 gene. *Nucleic Acids Res*, 23, 293-301.
36. Farber, S. A., Olson, E. S., Clark, J. D., and Halpern, M. E. (1999) Characterization of Ca2+-dependent phospholipase A2 activity during zebrafish embryogenesis. *J Biol Chem* 274, 19338-19346.
37. Cho, W., Han, S. K., Lee, B. I., Snitko, Y., and Dua, R. (1999) Purification and assay of mammalian group I and group IIa secretory phospholipase A2. *Methods in Molecular Biology* 109, 31-38.
38. Ouellette, A. J. (1997) Paneth cells and innate immunity in the crypt microenvironment. *Gastroenterology* 113, 1779-1784.
39. Lin, L., Lin, A., and Knopf, J. (1992) Cytosolic phospholipase A2 is coupled to hormonally regulated release of arachidonic acid. *Proc Natl Acad Sci USA* 89, 6147-6151.
40. Balsinde, J., and Dennis, E. (1997) Function and inhibition of intracellular calcium-independent phospholipase A2. *J Biol Chem* 272, 16069-16072.
41. Clark, J. D., Lin, L. L., Kriz, R. W., Ramesha, C. S., Sultzman, L. A., Lin, A. Y., Milona, N., and Knopf, J. L. (1991) A novel arachidonic acid-selective cytosolic $PLA_2$ contains a Ca(2+)-dependent translocation domain with homology to PKC and GAP. *Cell* 65, 1043-1051.
42. Rosenthal, M. D., Rzigalinski, B. A., Blackmore, P. F., and Franson, R. C. (1995) Cellular regulation of arachidonate mobilization and metabolism. *Prostaglandins Leukotrienes & Essential Fatty Acids* 52, 93-98.
43. Lambeau, G., and Lazdunski, M. (1999) Receptors for a growing family of secreted phospholipases A2. *Trends in Pharmacological Sciences* 20, 162-170.
44. Kramer, R. M., and Sharp, J. D. (1997) Structure, function and regulation of Ca2+-sensitive cytosolic phospholipase A2 ($cPLA_2$). *FEBS Letters* 410, 49-53.
45. Nalefski, E., Sultzman, L., Martin, D., Kriz, R., Towler, P., Knopf, J., and Clark, J. (1994) Delineation of two functionally distinct domains of cytosolic phospholipase A2, a regulatory Ca(2+)-dependent lipid-binding domain and a Ca(2+)-independent catalytic domain. *J Biol Chem* 269, 18239-18249.
46. Murakami, M., Shimbara, S., Kambe, T., Kuwata, H., Winstead, M., Tischfield, J., and Kudo, I. (1998) The functions of five distinct mammalian phospholipase A2 sin regulating arachidonic acid release. *Journal of Biological Chemistry* 273, 14411-14423.
47. Qiu, Z., Gijon, M., de, C. M., Spencer, D., and Leslie, C. (1998) The role of calcium and phosphorylation of cytosolic phospholipase A2 in regulating arachidonic acid release in macrophages. *J Biol Chem* 273, 8203-8211.
48. Garavito, R. M., and DeWitt, D. L. (1999) The cyclooxygenase isoforms: structural insights into the conversion of arachidonic acid to prostaglandins. *Biochimica et Biophysica Acta* 1441, 278-287.
49. Dubois, R. N., Abramson, S. B., Crofford, L., Gupta, R. A., Simon, L. S., Van De Putte, L. B., and Lipsky, P. E. (1998) Cyclooxygenase in biology and disease [see comments]. *FASEB Journal* 12, 1063-1073.
50. Scott, K. F., Bryant, K. J., and Bidgood, M. J. (1999) Functional coupling and differential regulation of the phospholipase A2-cyclooxygenase pathways in inflammation. *Journal of Leukocyte Biology* 66, 535-541.
51. Han, C., Ming, Z., and Lautt, W. W. (1999) Blood flow-dependent prostaglandin f(2alpha) regulates intestinal glucose uptake from the blood. *American Journal of Physiology* 277, G367-374.
52. Fink, M. P., Morrissey, P. E., Stein, K. L., Clement, R. E., Fiallo, V., and Gardiner, W. M. (1988) Systemic and regional hemodynamic effects of cyclooxygenase and thromboxane synthetase inhibition in normal and hyperdynamic endotoxemic rabbits. *Circulatory Shock* 26, 41-57.
53. Proctor, K. G. (1985) Differential effect of cyclooxygenase inhibitors on absorptive hyperemia. *American Journal of Physiology* 249, H755-762.
54. Chapnick, B. M. (1984) Divergent influences of leukotrienes C4, D4, and E4 on mesenteric and renal blood flow. *American Journal ofphysiology* 246, H518-524.
55. Davies, N. M. (1995) Toxicity of nonsteroidal anti-inflammatory drugs in the large intestine. *Diseases of the Colon & Rectum* 38, 1311-1321.
56. Tessner, T. G., Cohn, S. M., Schloemann, S., and Stenson, W. F. (1998) Prostaglandins prevent decreased epithelial cell proliferation associated with dextran sodium sulfate injury in mice. *Gastroenterology* 115, 874-882.
57. Schmassmann, A., Peskar, B. M., Stettler, C., Netzer, P., Stroff, T., Flogerzi, B., and Halter, F. (1998) Effects of inhibition of prostaglandin endoperoxide synthase-2 in chronic gastro-intestinal ulcer models in rats. *British Journal of Pharmacology* 123, 795-804.
58. Goodlad, R. A., Madgwick, A. J., Moffatt, M. R., Levin, S., Allen, J. L., and Wright, N. A. (1989) Prostaglandins and the gastric epithelium: effects of misoprostol on gastric epithelial cell proliferation in the dog. *Gut* 30, 316-321.
59. Reeves, M. J., Newcomb, P. A., Trentham-Dietz, A., Storer, B. E., and Remington, P. L. (1996) Nonsteroidal anti-inflammatory drug use and protection against colorectal cancer in women. *Cancer Epidemiology, Biomarkers & Prevention* 5, 955-960.
60. Thun, M. J. (1996) NSAID use and decreased risk of gastrointestinal cancers. *Gastroenterology Clinics of North America* 25, 333-348.
61. Smalley, W., Ray, W. A., Daugherty, J., and Griffin, M. R. (1999) Use of nonsteroidal anti-inflammatory drugs and 61. (cont.) incidence of colorectal cancer: a population-based study. *Archives of Internal Medicine* 159, 161-166.
62. Ritland, S. R., and Gendler, S. J. (1999) Chemoprevention of intestinal adenomas in the ApcMin mouse by piroxicam: kinetics, strain effects and resistance to chemosuppression. *Carcinogenesis* 20, 51-58.
63. Collet, J. P., Sharpe, C., Belzile, E., Boivin, J. F., Hanley, J., and Abenhaim, L. (1999) Colorectal cancer prevention by non-steroidal anti-inflammatory drugs: effects of dosage and timing [see comments]. *British Journal of Cancer* 81, 62-68.
64. Coogan, P. F., Rosenberg, L., Palmer, J. R., Strom, B. L., Zauber, A. G., Stolley, P. D., and Shapiro, S. (2000) Non-steroidal anti-inflammatory drugs and risk of digestive cancers at sites other than the large bowel. *Cancer Epidemiology, Biomarkers & Prevention* 9, 119-123.
65. de Jong, T. A., Skinner, S. A., Malcontenti-Wilson, C., Vogiagis, D., Bailey, M., van Driel, I. R., and O Brien, P. E. (2000) Inhibition of rat colon tumors by sulindac and sulindac sulfone is independent of K-ras (codon 12) mutation. *American Journal of Physiology—Gastrointestinal & Liver Physiology* 278, G266-272.
66. Cormier, R. T., Hong, K. H., Halberg, R. B., Hawkins, T. L., Richardson, P., Mulherkar, R., Dove, W. F., and Lander, E. S. (1997) Secretory phospholipase Pla2g2a confers resistance to intestinal tumorigenesis [see comments]. *Nature Genetics* 17, 88-91.
67. Praml, C., Savelyeva, L., Le Paslier, D., Siracusa, L. D., Buchberg, A. M., Schwab, M., and Amler, L. C. (1995) Human homologue of a candidate for the Mom1 locus, the secretory type II phospholipase A2 (PLA2S-II), maps to 1p35-36.1/D1S199. *Cancer Research* 55, 5504-5506.
68. MacPhee, M., Chepenik, K. P., Liddell, R. A., Nelson, K. K., Siracusa, L. D., and Buchberg, A. M. (1995) The secretory phospholipase A2 gene is a candidate for the Mom1 locus, a major modifier of ApcMin-induced intestinal neoplasia. *Cell* 81, 957-966.
69. Oshima, M., Dinchuk, J. E., Kargman, S. L., Oshima, H., Hancock, B., Kwong, E., Trzaskos, J. M., Evans, J. F., and Taketo, M. M. (1996) Suppression of intestinal polyposis in Apc delta716 knockout mice by inhibition of cyclooxygenase 2 (COX-2). *Cell* 87, 803-809.
70. Fourcade, O., Simon, M., Viode, C., Rugani, N., Leballe, F., Ragab, A., Fournie, B., Sarda, L., and Chap, H. (1995) Secretory phospholipase A2 generates the novel lipid mediator lysophosphatidic acid in membrane microvesicles shed from activated cells. *Cell* 80, 919-927.
71. Balsinde, J., and Dennis, E. (1996) Distinct roles in signal transduction for each of the phospholipase A2 enzymes present in P388D1 macrophages. *J Biol Chem* 271, 6758-6765.
72. Green, J. A., Smith, G. M., Buchta, R., Lee, R., Ho, K. Y., Rajkovic, I. A., and Scott, K. F. (1991) Circulating phospholipase A2 activity associated with sepsis and septic shock is indistinguishable from that associated with rheumatoid arthritis. *Inflammation* 15, 355-367.
73. Henderson, W. R., Jr. (1994) The role of leukotrienes in inflammation. [Review] *Ann Intern Med* 121, 684-697.
74. Larsen, G., and Henson, P. (1983) Mediators of inflammation. *Annu Rev Immunol* 1, 335-359.
75. Malo, P. E., Bell, R. L., Shaughnessy, T. K., Summers, J. B., Brooks, D. W., and Carter, G. W. (1994) The 5-lipoxygenase inhibitory activity of zileuton in in vitro and in vivo models of antigen-induced airway anaphylaxis. *Pulm Pharmacol* 7, 73-79.
76. Nevalainen, T. J. (1993) Serum phospholipases A2 in inflammatory diseases. [Review]. *Clin Chem* 39, 2453-2459.
77. Murakami, M., Kambe, T., Shimbara, S., and Kudo, I. (1999) Functional coupling between various phospholipase A2s and cyclooxygenases in immediate and delayed prostanoid biosynthetic pathways. *Journal of Biological Chemistry* 274, 3103-3115.
78. Hanasaki, K., Yokota, Y., Ishizaki, J., Itoh, T., and Arita, H. (1997) Resistance to endotoxic shock in phospholipase A2 receptor-deficient mice. *J Biol Chem* 272, 32792-32797.
79. Cupillard, L., Mulherkar, R., Gomez, N., Kadam, S., Valentin, E., Lazdunski, M., and Lambeau, G. (1999) Both group IB and group IIA secreted phospholipases A2 are natural ligands of the mouse 180-kDa M-type receptor. *Journal of Biological Chemistry* 274, 7043-7051.
80. Shoda, J., Kano, M., Asano, T., Irimura, T., Ueda, T., Iwasaki, R., Furukawa, M., Kamiya, J., Nimura, Y., Todoroki, T., Matsuzaki, Y., and Tanaka, N. (1999) Secretory low-molecular-weight phospholipases A2 and their specific receptor in bile ducts of patients with intrahepatic calculi: factors of chronic proliferative cholangitis. *Hepatology* 29, 1026-1036.
81. Murata, K., Egami, H., Kiyohara, H., Oshima, S., Kurizaki, T., and Ogawa, M. (1993) Expression of group-II phospholipase A2 in malignant and non-malignant human gastric mucosa. *Br J Cancer* 68, 103-111.
82. Tocher, D. (1995) Glycerophospholipid metabolism. *In Biochemistry and Molecular Biology of Fishes* (Hochachka, P., and Mommsen, T., eds) Vol. 4 pp. 119-157, Elsevier, N.Y.
83. Mayer, R. J., and Marshall, L. A. (1993) New insights on mammalian phospholipase A2(s); comparison of arachidonoyl-selective and -nonselective enzymes. *FASEB Journal* 7, 339-348.
84. Murata, K., Egami, H., Kiyohara, H., Oshima, S., Kurizaki, T., and Ogawa, M. (1993) Expression of group-II phospholipase A2 in malignant and non-malignant human gastric mucosa. *British Journal of Cancer* 68, 103-111.
85. Li, L., Wang, Y. P., Capparelli, A. W., Jo, O. D., and Yanagawa, N. (1994) Effect of luminal angiotensin II on proximal tubule fluid transport: role of apical phospholipase A2. *American Journal of Physiology* 266, F202-209.
86. Gassama-Diagne, A., Rogalle, P., Fauvel, J., Willson, M., Klaebe, A., and Chap, H. (1992) Substrate specificity of phospholipase B from guinea pig intestine. A glycerol ester lipase with broad specificity. *Journal of Biological Chemistry* 267, 13418-13424.
87. Delagebeaudeuf, C., Gassama-Diagne, A., Nauze, M., Ragab, A., Li, R. Y., Capdevielle, J., Ferrara, P., Fauvel, J., and Chap, H. (1998) Ectopic epididymal expression of guinea pig intestinal phospholipase B. Possible role in sperm maturation and activation by limited proteolytic digestion. *Journal of Biological Chemistry* 273, 13407-13414.
88. Tojo, H., Ichida, T., and Okamoto, M. (1998) Purification and characterization of a catalytic domain of rat intestinal phospholipase B/lipase associated with brush border membranes. *Journal of Biological Chemistry* 273, 2214-2221.
89. Boll, W., Schmid-Chanda, T., Semenza, G., and Mantei, N. (1993) Messenger RNAs expressed in intestine of adult but not baby rabbits. Isolation of cognate cDNAs and characterization of a novel brush border protein with esterase and phospholipase activity. *Journal of Biological Chemistry* 268, 12901-12911.
90. Spector, A. A. (1984) Plasma lipid transport. *Clinical Physiology & Biochemistry* 2, 123-134.

91. Glatz, J. F., and van der Vusse, G. J. (1989) Intracellular transport of lipids. *Molecular & Cellular Biochemistry* 88, 37-44.
92. Tso, P., Liu, M., and Kalogeris, T. J. (1999) The role of apolipoprotein A-IV in food intake regulation. *Journal of Nutrition* 129, 1503-1506.
93. Hendrickson, H. S. (1994) Fluorescence-based assays of lipases, phospholipases, and other lipolytic enzymes. [Review]. *Anal Biochem* 219, 1-8.
94. Hendrickson, H. S., Hendrickson, E. K., Johnson, I. D., and Farber, S. A. (1999) Intramolecularly quenched BODIPY-labeled phospholipid analogs in phospholipase A(2) and platelet-activating factor acetylhydrolase assays and in vivo fluorescence imaging. *Anal Biochem* 276, 27-35.
95. Honkanen, R. E., Rigler, M. W., and Patton, J. S. (1985) Dietary fat assimilation and bile salt absorption in the killifish intestine. *American Journal of Physiology* 249, G399-407.
96. Dennis, E. (1994) Diversity of group types, regulation, and function of phospholipase A2. *J Biol Chem* 269, 13057-13060.
97. Folch, J., Lees, M., and Sloane Stanley, G. (1957) A simple method for the isolation and purification of total lipids from animal tissues. *J. Biol. Chem.* 226, 497-509.
98. Touchstone, J., Chen, J., and Beaver, K. (1980) Improved separation of phospholipids in thin layer chromatography. *Lipids* 15, 61-62.
99. R. E. Pagano, D. K. S. a. A. J. S. (1980) Introduction of phospholipids into mammalian cell surfaces via lipid vesicles. *In Lipisomes and Immunobiology* (Six, B. H. T. a. H. R., ed) pp. 193-210, Elsevier, N.Y.
100. Brockman, H. (2000) 44th Annual meeting of the Biophysical Society. New Orleans, La., USA. Feb. 12-16, 2000. Abstract #1060. *Biophys J* 78, 1 A-545A.
101. Farber, S. A., Buyukuysal, R. L., and Wurtman, R. J. (1991) Why do phospholipid levels decrease with repeated stimulation? A study of choline-containing compounds in rat striatum following electrical stimulation. *Ann NY Acad Sci* 640, 114-117.
102. Farber, S. A., Savci, V., Wei, A., Slack, B. E., and Wurtman, R. J. (1996) Choline s phosphorylation in rat striatal slices is regulated by the activity of cholinergic neurons. *Brain Res* 723, 90-99.
103. Westerfield, M. (1995) *The Zebrafish Book*, University of Oregon, Eugene.
104. Hukriede, N., Joly, L., Tsang, M., Miles, J., Tellis, P., Epstein, J., Barbazuk, W., Li, F., Paw, B., Postlethwait, J., Hudson, T., Zon, L., McPherson, J., Chevrette, M., Dawid, I., Johnson, S., and Ekker, M. (1999) Radiation hybrid mapping of the zebrafish genome. *Proc Natl Acad Sci USA* 96, 9745-9750.
105. Sheridan, M. A. (1988) *Comp. Biochem. Physiol. B* 90, 679.
106. Hendrickson, H. S. (1994) *Anal. Biochem.* 219, 1.
107. Stroband, H. W., van deer Meer, H., and Timmermans, L. P. (1979) *Histochemistry* 64, 235.
108. Nawrocki et al., (1995) *Arterioscler. Thromb. Vasc. Biol.* 15, 678.
109. Goto, T. et al., (1997) *Hepatology* 26, 295A.

What is claimed is:

1. A method of identifying a test compound or agent affecting lipid or cholesterol metabolism, or a combination thereof, in a vertebrate's digestive system by a screening assay in a teleost, the method comprising:

providing a teleost, wherein organs of the teleost's digestive system are optically visible, permitting fluorescence contained therein to be seen directly;

bathing the teleost in media comprising the test compound or agent, such that the test compound or agent is ingested or absorbed by the teleost in vivo;

covalently linking a quenched or unquenched fluorescent moiety to the lipid or cholesterol, or combination thereof, being assayed in the teleost, such that the resulting labeled lipid or cholesterol is absorbed by the teleost's digestive system or function as substrates for target enzymes in the teleost's digestive system without impeding enzyme-substrate interaction;

bathing the teleost in media comprising the labeled lipid or cholesterol, or a combination thereof, such that the labeled lipid or cholesterol is ingested or absorbed by the teleost in vivo, and uptake is seen in its digestive system; then screening for and detecting accumulated fluorescence in the digestive organs of the teleost as an indicator of a modulating effect of the ingested test compound or agent on the metabolic processing of the labeled lipid or cholesterol in the digestive system of the teleost; then quantifying intensity and rate of fluorescence in the processed or unprocessed fluorescently labeled lipid or cholesterol in the digestive organs of the screened teleost as compared to a wild-type teleost; and providing a readout of digestive organ function, physiology of the digestive system and organs, or metabolic lipid or cholesterol metabolism or processing, or combinations thereof, of the screened teleost, wherein differences in the intensity or rate of the fluorescence in the screened teleost, when compared with the teleost prior to uptake of the test compound or agent or with the wild-type teleost, indicates the modulating effect of the test compound or agent on lipid or cholesterol metabolism, or a combination thereof, in the vertebrate's digestive system.

2. The method of claim 1, wherein the fluorescently labeled lipid or cholesterol is selected from phospholipase A2 (PLA2) substrates.

3. The method of claim 1, wherein the fluorescently labeled lipid reporters are selected from the group consisting of quenched or unquenched fluorescent phosphatidylcholine (PC) analogues, and quenched or unquenched fluorescent fatty acids or triglycerides.

4. The method of claim 3, wherein the quenched PC analogue is PED6.

5. The method of claim 1, wherein the cholesterol is NBD-labeled or BODIPY-labeled.

6. The method of claim 1, wherein the vertebrate is an intact, viable teleost.

7. The method of claim 6, wherein the teleost is an intact, viable zebrafish.

8. The method of claim 7, wherein the zebrafish is a zebrafish larvae, embryo or adult.

9. The method of claim 1, comprising detecting and quantifying the amount of processed or unprocessed fluorescently labeled lipid or cholesterol, when combined with the test compound or agent in the teleost's stomach, intestine, liver, pancreas, biliary tract, gall bladder, blood, serum, or combinations thereof.

10. The method of claim 9, further comprising applying the quantified findings in the teleost regarding the effects of modulating lipid or cholesterol processing, or combination thereof, or uptake to humans or non-human vertebrates.

11. The method of claim 1, wherein quantifying the resulting fluorescence of the labeled lipid or cholesterol, as reported following uptake of the test compound or agent in the digestive organs of the teleost, comprises a high-throughput screen for identifying and characterizing compounds or agents that effectively modulate lipid or cholesterol metabolism, or a combination thereof, in vivo in a vertebrate's digestive system.

12. The method of claim 11, wherein the modulating effect of the test compound or agent on lipid or cholesterol processing, or combination thereof, or uptake in the teleost's digestive system is visualized as organ-specific, accumulated fluorescence in the teleost's stomach, intestine, liver, pancreas, biliary tract, gall bladder, blood, serum, or combinations thereof.

13. The method of claim 11, further comprising applying the quantified findings in the teleost regarding the effects of modulating lipid or cholesterol processing, or combination thereof, or uptake to humans or non-human vertebrates.

14. The method of claim 1, wherein the teleost has mutation(s) in one or more genes required for digestive system development or physiology or lipid metabolism, and quantifying the resulting fluorescence in the digestive organs of the teleost comprises a high-through-put screen for determining the modulating effect of the test compound or agent on the mutations of specific genes, or expression thereof, that lead to or result in disorders of the teleost's digestive development or physiology or lipid or cholesterol metabolism, or combination thereof.

15. The method of claim 14, wherein the modulating effect on lipid or cholesterol processing, or combination thereof, or uptake in the teleost's digestive system is visualized as organ-specific, accumulated fluorescence in the stomach, intestine, liver, pancreas, biliary tract, gall bladder, blood, serum, or combinations thereof.

16. The method of claim 14, further comprising applying the quantified findings in the teleost regarding the effects of modulating lipid or cholesterol processing, or combination thereof, or uptake in the digestive system to humans or non-human vertebrates.

17. The method of claim 1, wherein the teleost has a diseased, aberrant or abnormal digestive system or disrupted lipid metabolism, and quantifying the modulating effect of the test compound or agent on the labeled lipid or cholesterol, or combination thereof, by screening the resulting fluorescence in the teleost's digestive organs comprises a high-through-put screen for identifying or characterizing compounds or agents that effectively modulate lipid or cholesterol metabolism, or a combination thereof, in vivo in a vertebrate's digestive system.

18. The method of claim 17, further comprising applying the quantified findings in the teleost regarding the effects of modulating lipid or cholesterol processing, or combination thereof, or uptake in the digestive system to humans or non-human vertebrates.

19. The method of claim 1, wherein lipid or cholesterol absorption, or a combination thereof, in the teleost is enhanced in the presence of the test compound or agent.

20. The method of claim 1, wherein lipid or cholesterol absorption, or a combination thereof, in the teleost is reduced in the presence of the test compound or agent.

* * * * *